(12) United States Patent
Gil et al.

(10) Patent No.: US 12,357,347 B2
(45) Date of Patent: Jul. 15, 2025

(54) FULCRUM FOR TARSAL-METATARSAL JOINT PROCEDURE

(71) Applicant: Treace Medical Concepts, Inc., Ponte Vedra, FL (US)

(72) Inventors: Carlos Eduardo Gil, Memphis, TN (US); Joe William Ferguson, Ponte Vedra Beach, FL (US)

(73) Assignee: Treace Medical Concepts, Inc., Ponte Vedra, FL (US)

(*) Notice: Subject to any disclaimer, the term of this patent is extended or adjusted under 35 U.S.C. 154(b) by 35 days.

(21) Appl. No.: 17/173,357

(22) Filed: Feb. 11, 2021

(65) Prior Publication Data

US 2021/0251659 A1    Aug. 19, 2021

Related U.S. Application Data

(62) Division of application No. 15/905,495, filed on Feb. 26, 2018, now Pat. No. 10,939,939.

(60) Provisional application No. 62/463,722, filed on Feb. 26, 2017.

(51) Int. Cl.
*A61B 17/56* (2006.01)
*A61B 17/02* (2006.01)

(52) U.S. Cl.
CPC ............ *A61B 17/56* (2013.01); *A61B 17/025* (2013.01); *A61B 2017/565* (2013.01)

(58) Field of Classification Search
CPC .............................. A61B 17/56; A61B 17/025
See application file for complete search history.

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,338,927 A | 7/1982 | Volkov et al. |
| 4,570,624 A | 2/1986 | Wu |
| 4,627,425 A | 12/1986 | Reese |
| 4,628,919 A | 12/1986 | Clyburn |
| 4,754,746 A | 7/1988 | Cox |

(Continued)

FOREIGN PATENT DOCUMENTS

| | | |
|---|---|---|
| AU | 2009227957 B2 | 7/2014 |
| CA | 2491824 A1 | 9/2005 |

(Continued)

OTHER PUBLICATIONS

Defendant Fusion Orthopedics LLC's Invalidity Contentions, No. CV-22-00490-PHX-SRB, US District Court for the District of Arizona, Aug. 27, 2022, 41 pages.

(Continued)

*Primary Examiner* — Sameh R Boles
(74) *Attorney, Agent, or Firm* — Fredrikson & Byron, P.A.

(57) ABSTRACT

A technique for correcting a bone deformity, such as a bunion, may be performed using a fulcrum. In some examples, the fulcrum includes multiple members that are joined together at one end and spaced apart from each other at an opposite end. The fulcrum members can be manipulated to adjust the distance separating the fulcrum members from each other and, correspondingly, an amount of force separating the multiple members from each other. The force can be controlled to press against opposed bones, such as first and second metatarsals in an intermetatarsal space.

17 Claims, 16 Drawing Sheets

(56) References Cited

U.S. PATENT DOCUMENTS

| | | |
|---|---|---|
| 4,757,810 A | 7/1988 | Reese |
| 4,895,141 A | 1/1990 | Koeneman et al. |
| 4,952,214 A | 8/1990 | Comparetto |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,112,334 A | 5/1992 | Alchermes et al. |
| 5,207,676 A | 5/1993 | Canadell et al. |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,413,579 A | 5/1995 | Tom Du Toit |
| 5,417,694 A | 5/1995 | Marik et al. |
| 5,449,360 A | 9/1995 | Schreiber |
| 5,529,075 A | 6/1996 | Clark |
| 5,586,564 A | 12/1996 | Barrett et al. |
| 5,601,565 A | 2/1997 | Huebner |
| 5,620,442 A | 4/1997 | Bailey et al. |
| H1706 H | 1/1998 | Mason |
| 5,788,695 A | 8/1998 | Richardson |
| 5,803,924 A | 9/1998 | Oni et al. |
| 5,810,822 A | 9/1998 | Mortier |
| 5,893,553 A | 4/1999 | Pinkous |
| 5,935,128 A | 8/1999 | Carter et al. |
| 5,941,877 A | 8/1999 | Viegas et al. |
| 5,951,556 A | 9/1999 | Faccioli et al. |
| 6,030,391 A | 2/2000 | Brainard et al. |
| 6,162,223 A | 12/2000 | Orsak et al. |
| 6,171,309 B1 | 1/2001 | Huebner |
| 6,416,465 B2 | 7/2002 | Brau |
| 6,511,481 B2 | 1/2003 | Von Hoffmann et al. |
| 6,719,773 B1 | 4/2004 | Boucher et al. |
| 6,743,233 B1 | 6/2004 | Baldwin et al. |
| 7,033,361 B2 | 4/2006 | Collazo |
| 7,097,647 B2 | 8/2006 | Segler et al. |
| 7,153,310 B2 | 12/2006 | Ralph et al. |
| 7,182,766 B1 | 2/2007 | Mogul |
| 7,241,298 B2 | 7/2007 | Nemec et al. |
| 7,326,218 B2 * | 2/2008 | Sterett ............. A61B 17/025 600/587 |
| 7,377,924 B2 | 5/2008 | Raistrick et al. |
| 7,465,303 B2 | 12/2008 | Riccione et al. |
| 7,641,660 B2 | 1/2010 | Lakin et al. |
| D610,257 S | 2/2010 | Horton |
| 7,686,811 B2 | 3/2010 | Byrd et al. |
| D629,900 S | 12/2010 | Fisher |
| 7,972,338 B2 | 7/2011 | O'Brien |
| D646,389 S | 10/2011 | Claypool et al. |
| 8,057,478 B2 | 11/2011 | Kuczynski et al. |
| D651,315 S | 12/2011 | Bertoni et al. |
| D651,316 S | 12/2011 | May et al. |
| 8,080,010 B2 | 12/2011 | Schulz et al. |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,246,561 B1 | 8/2012 | Agee et al. |
| D666,721 S | 9/2012 | Wright et al. |
| 8,262,664 B2 | 9/2012 | Justin et al. |
| 8,282,644 B2 | 10/2012 | Edwards |
| 8,282,645 B2 | 10/2012 | Lawrence et al. |
| 8,292,966 B2 | 10/2012 | Morton |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Bscher |
| D679,395 S | 4/2013 | Wright et al. |
| 8,435,246 B2 | 5/2013 | Fisher et al. |
| 8,475,462 B2 | 7/2013 | Thomas et al. |
| 8,523,870 B2 | 9/2013 | Green, II et al. |
| D694,884 S | 12/2013 | Mooradian et al. |
| D695,402 S | 12/2013 | Dacosta et al. |
| 8,652,142 B2 | 2/2014 | Geissler |
| D701,303 S | 3/2014 | Cook |
| 8,672,945 B2 | 3/2014 | Lavallee et al. |
| 8,696,716 B2 | 4/2014 | Kartalian et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,763 B2 | 7/2014 | Wong et al. |
| 8,771,279 B2 | 7/2014 | Philippon et al. |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | Dacosta et al. |
| 9,750,538 B2 | 9/2017 | Soffiatti et al. |
| 9,980,760 B2 | 5/2018 | Dacosta et al. |
| 10,376,268 B2 | 8/2019 | Fallin et al. |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0198531 A1 | 12/2002 | Millard et al. |
| 2003/0195516 A1 | 10/2003 | Sterett et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2005/0004676 A1 | 1/2005 | Schon et al. |
| 2005/0059978 A1 | 3/2005 | Sherry et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0267482 A1 | 12/2005 | Hyde, Jr. |
| 2005/0273112 A1 | 12/2005 | McNamara |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0091197 A1 | 4/2008 | Coughlin |
| 2008/0140081 A1 | 6/2008 | Heavener et al. |
| 2008/0172054 A1 | 7/2008 | Claypool et al. |
| 2008/0208252 A1 | 8/2008 | Holmes |
| 2008/0262500 A1 | 10/2008 | Collazo |
| 2008/0269908 A1 | 10/2008 | Warburton |
| 2009/0036893 A1 | 2/2009 | Kartalian et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |

(56) References Cited

U.S. PATENT DOCUMENTS

| | | |
|---|---|---|
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0324556 A1 | 12/2010 | Tyber et al. |
| 2011/0093084 A1 | 4/2011 | Morton |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130383 A1 | 5/2012 | Budoff |
| 2012/0184961 A1 | 7/2012 | Johannaber |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee et al. |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0096563 A1 | 4/2013 | Meade et al. |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0194884 A1 | 7/2014 | Martin et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton et al. |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0354127 A1 | 12/2016 | Lundquist et al. |
| 2017/0014173 A1* | 1/2017 | Smith ................ A61B 17/8866 |
| 2017/0042598 A1 | 2/2017 | Santrock et al. |
| 2017/0042599 A1 | 2/2017 | Bays et al. |
| 2017/0079669 A1 | 3/2017 | Bays et al. |
| 2018/0132868 A1 | 5/2018 | Dacosta et al. |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| EP | 685206 B1 | 9/2000 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 3023068 A2 | 5/2016 |
| FR | 2362616 A1 | 3/1978 |
| FR | 2764183 B1 | 11/1999 |
| FR | 3030221 A1 | 6/2016 |
| GB | 2154143 A | 9/1985 |
| GB | 2154144 A | 9/1985 |
| IN | 200903719 P1 | 6/2009 |
| IN | 200904479 P2 | 5/2010 |
| IN | 140/DELNP/2012 P1 | 2/2013 |

(56) References Cited

FOREIGN PATENT DOCUMENTS

| | | |
|---|---|---|
| IN | 2004/KOLNP/2013 P2 | 11/2013 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015105880 A1 | 7/2015 |
| WO | 2015127515 A2 | 9/2015 |

OTHER PUBLICATIONS

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.

Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, U.S. Appl. No. 62/118,378, filed Feb. 19, 2015, 62 pages.
Fishco, "A Straightforward Guide to the Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.

(56) References Cited

OTHER PUBLICATIONS

Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus," The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation for Nonunions: What the Evidence Reveals," Podiatry Today, vol. 24, No. 9, Sep. 2011, pp. 52-57.

Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.

(56) References Cited

OTHER PUBLICATIONS

DeCarbo et al., "Resurfacing Interpositional Arthroplasty for Degenerative Joint Diseas of the First Metatarsalphalangeal Joint," Podiatry Management, Jan. 2013, pp. 137-142.

DeCarbo et al., "Locking Plates: Do They Prevent Complications?," Podiatry Today, Apr. 2014, 7 pages.

Easley et al., "Current Concepts Review: Hallux Valgus Part II: Operative Treatment," Foot and Ankle International, vol. 28, No. 6, Jun. 2007, pp. 748-758.

Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Easley et al., "What is the Best Treatment for Hallux Valgus?," Evidence-Based Orthopaedics—The Best Answers to Clinical Questions, Chapter 73, 2009, pp. 479-491.

Shurnas et al., "Proximal Metatarsal Opening Wedge Osteotomy," Operative Techniques in Foot and Ankle Surgery, Section I, Chapter 13, 2011, pp. 73-78.

Coetzee et al., "Revision Hallux Valgus Correction," Operative Techniques in Foot and Ankle Surgery, Section I, Chapter 15, 2011, pp. 84-96.

Le et al., "Tarsometatarsal Arthrodesis," Operative Techniques in Foot and Ankle Surgery, Section II, Chapter 40, 2011, pp. 281-285.

Collan et al., "The biomechanics of the first metatarsal bone in hallux valgus: A preliminary study utilizing a weight bearing extremity CT," Foot and Ankle Surgery, vol. 19, 2013, pp. 155-161.

Eustace et al., "Hallux valgus, first metatarsal pronation and collapse of the medial longitudinal arch—a radiological correlation," Skeletal Radiology, vol. 23, 1994, pp. 191-194.

Mizuno et al., "Detorsion Osteotomy of the First Metatarsal Bone in Hallux Valgus," Japanese Orthopaedic Association, Tokyo, 1956; 30:813-819.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.

D'Amico et al., "Motion of the First Ray: Clarification Through Investigation," Journal of the American Podiatry Association, vol. 69, No. 1, Jan. 1979, pp. 17-23.

Groves, "Operative Report," St. Tammany Parish Hospital, Date of Procedure, Mar. 26, 2014, 2 pages.

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

Anderson et al., "Uncemented STAR Total Ankle Prostheses," The Journal of Bone and Joint Surgery, vol. 86(1, Suppl 2), Sep. 2004, pp. 103-111, (Abstract Only).

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Garthwait, "Accu-Cut System Facilitates Enhanced Precision," Podiatry Today, vol. 18, No. 6, Jun. 2005, 6 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).

"Hat-Trick Lesser Toe Repair System," Smith & Nephew, Brochure, Aug. 2014, 12 pages.

"Hoffmann II Compact External Fixation System," Stryker, Brochure, Literature No. 5075-1-500, 2006, 12 pages.

"Hoffmann II Micro Lengthener," Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

"Lag Screw Target Bow," Stryker Leibinger GmbH & Co. KG, Germany 2004, 8 pages.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Michelangelo Bunion System, Surgical Technique, Instratek Incorporated, publication date unknown, 4 pages.

Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.

Modular Rail System: External Fixator, Smith & Nephew, Surgical Technique, 2013, 44 pages.

(56) References Cited

OTHER PUBLICATIONS

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Rx-Fix Mini Rail External Fixator, Wright Medical Technology, Brochure, Aug. 15, 2014, 2 pages.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation of Metatarsal Fracture With Bone Plate in a Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Stableloc External Fixation System, Acumed, Product Overview, Effective date Sep. 2015, 4 pages.
Stahl et al., "Derotation of Post-Traumatic Femoral Deformities by Closed Intramedullary Sawing," Injury, vol. 37, No. 2, Feb. 2006, pp. 145-151, (Abstract Only).
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Weber et al., "A Simple System for Navigation of Bone Alignment Osteotomies of the Tibia," International Congress Series, vol. 1268, Jan. 2004, pp. 608-613, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.

\* cited by examiner

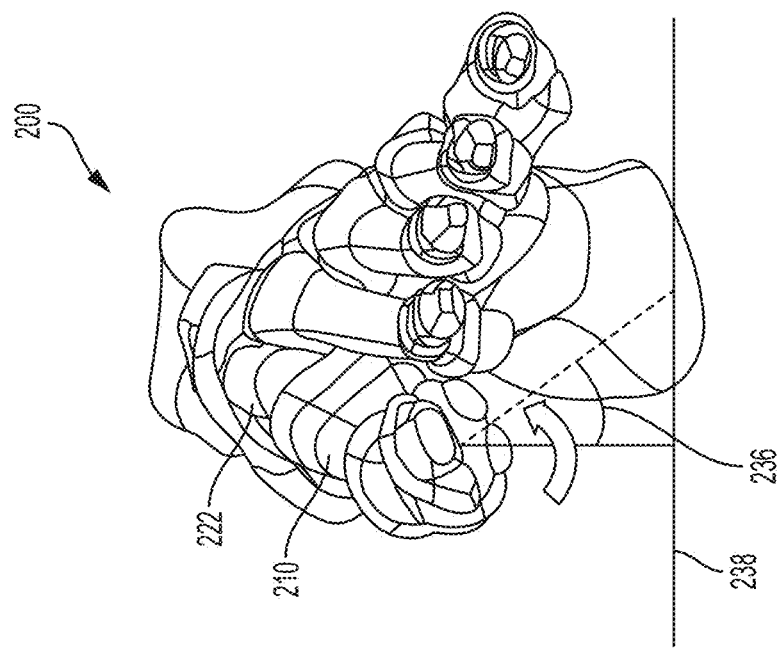
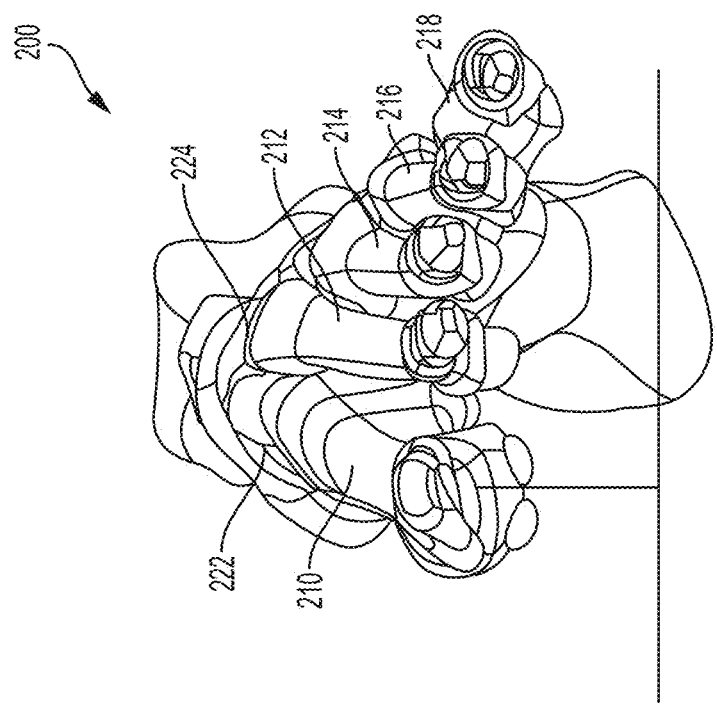
FIG. 1A
FIG. 1B

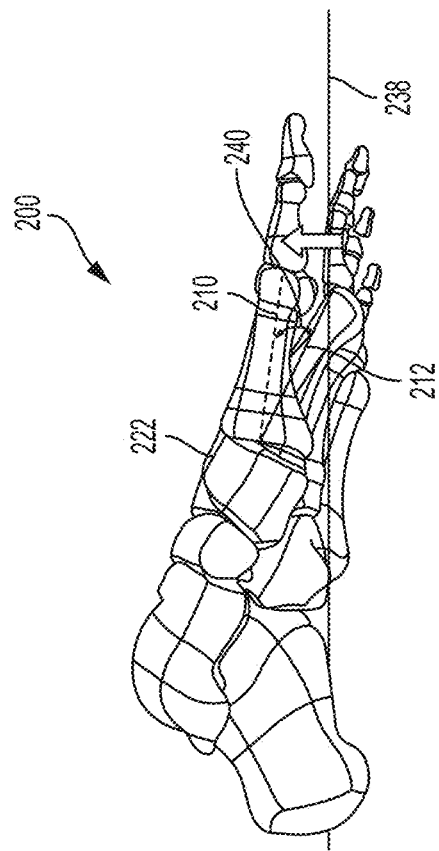
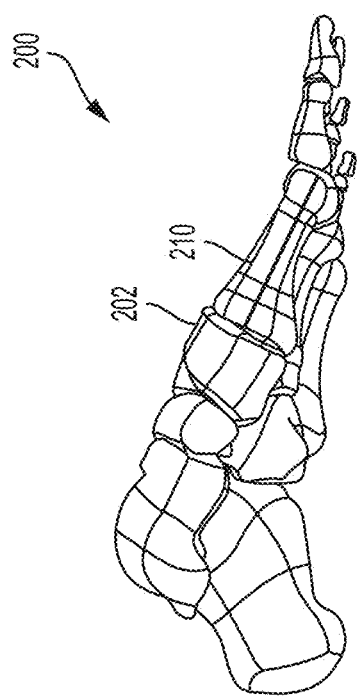
FIG. 3B
FIG. 3A

FULCRUM FOR TARSAL-METATARSAL JOINT PROCEDURE

RELATED APPLICATIONS

This application is a divisional of U.S. application Ser. No. 15/905,495, filed Feb. 26, 2018, which claims the benefit of U.S. Provisional Application No. 62/463,722, filed Feb. 26, 2017. The entire contents of each application are incorporated herein by reference.

TECHNICAL FIELD

This disclosure relates to surgical devices and, more particularly, to surgical devices for assisting in bone realignment techniques.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is medially deviated, resulting in an abduction of the first metatarsal while the phalanges adduct. This often leads to development of soft tissue and a bony prominence on the medial side of the foot, which is called a bunion.

Surgical intervention may be used to correct a bunion deformity. A variety of different surgical procedures exist to correct bunion deformities and may involve removing the abnormal bony enlargement on the first metatarsal and/or attempting to realign the first metatarsal relative to the adjacent metatarsal. Surgical instruments that can facilitate efficient, accurate, and reproducible clinical results are useful for practitioners performing bone realignment techniques.

SUMMARY

In general, this disclosure is directed to a fulcrum that can be used in a surgical bone realignment procedure. The fulcrum may be configured (e.g., sized and/or shaped) to be positioned in an intermetatarsal space between adjacent metatarsals, such as in the intermetatarsal space between the first metatarsal and the second metatarsal. The fulcrum can be configured to self-retain within the intermetatarsal space once inserted. For example, the fulcrum may be composed of two members that have a force biasing them away from each other. Once inserted into the intermetatarsal space, one member of the fulcrum may press against the first metatarsal while the second member presses against the second metatarsal. The force biasing the two members of the fulcrum away from each other may be effective to retain the fulcrum in the intermetatarsal space without substantially moving in the dorsal to plantar direction. This can be useful to help prevent the fulcrum from moving once inserted into the intermetatarsal space, allowing bones to be moved relative to the fulcrum without requiring a clinician performing a bone realignment procedure to hold and/or reposition the fulcrum because of inadvertent movement.

In one example, a self-retaining fulcrum is configured with two members joined together. The two members can be manipulated to increase a separation distance between the members. The opposite end of the two members from the joint can be compressed or squeezed together to facilitate insertion of the fulcrum into the joint space between two bones. Upon releasing the force compressing the two members together, a spring force created by the junction between the two members may push the members outwardly away from each other. This may provide a force on each member of the fulcrum, forcing the members against opposite bones in which they are in contact, which may help retain the fulcrum within the joint space.

In another example, a self-retaining fulcrum may be configured with two members that are rotatably coupled together. Before or after the fulcrum is inserted into a desired space between opposed bones, one member of the fulcrum may be rotated relative to the other member of the fulcrum to expand the cross-sectional size of the fulcrum. This may provide a force helping to retain the fulcrum in the space between the opposed bones.

Independent of the specific configuration of the fulcrum, one or more surfaces of the fulcrum may have surface features configured to facilitate and/or inhibit directional movement. For example, the outward facing surface of the fulcrum configured to be positioned in contact with the first metatarsal may have surface features that allow the first metatarsal to be rotated in the frontal plane but that inhibit movement of the fulcrum in the dorsal to plantar direction. Additionally or alternatively, the outward facing surface of the fulcrum configured to be positioned in contact with the second metatarsal may have surface features that inhibit movement of the fulcrum in the proximal to distal direction and/or the dorsal to plantar direction.

In use, the two members of the fulcrum may be brought in close proximity to provide a structure of compact cross-sectional area for insertion into an intermetatarsal space. For example, when the fulcrum includes two members that are rotatably connected together, one member may be rotated to a closed position (or may be initially provided, for example directly from a package, in a closed position). As another example, when the fulcrum includes two members fixedly and/or compressibility connected together, the un-joined ends of the two members may be compressed towards each other to provide a fulcrum structure of reduced cross-sectional area. In either case, the fulcrum can be inserted into an intermetatarsal space between a first metatarsal and a second metatarsal, such that one member of the fulcrum contacts the first metatarsal and the other member of the fulcrum contacts the second metatarsal. Thereafter, the fulcrum can be expanded, e.g., by rotating one member relative to another member or by releasing the compression holding the free ends of the fulcrum together. The resulting force provided by the opposed ends of the fulcrum being biased away from each other can be effective to retain the fulcrum in the intermetatarsal space without substantially moving (e.g., in a dorsal to plantar direction). Thereafter, the clinician may perform a bone realignment procedure that involves moving the first metatarsal in one or more planes relative to a medial cuneiform and/or the second metatarsal to correct the anatomical misalignment of the first metatarsal. As the clinician moves the first metatarsal, the fulcrum may provide a pivot point about which the first metatarsal can translate and/or rotate. In this way, the fulcrum can provide a fulcrum functionality for movement of the first metatarsal.

In one example, a fulcrum for use in a bone realignment procedure is described. The fulcrum includes a body and a handle. The body is configured to be inserted in an intermetatarsal space between adjacent metatarsals. The handle is operatively connected to the body. The example specifies that the body includes a first member having a length extending from a first end to a second end and a second member having a length extending from a first end to a second end. The first end of the second member is coupled to the first member and the second end of the second member is movable toward and away from the first member such that a thickness of the body between the first member and the second member is adjustable. Additionally, the handle projects at a non-zero degree angle from the body to define a tissue retraction space between the handle and the body.

In another example, a method is described that involves inserting a fulcrum body that includes a first member and a second member between a first metatarsal and a second metatarsal such that the first member contacts the second metatarsal and the second member contacts the first metatarsal, where the first metatarsal is anatomically misaligned with respect to the second metatarsal. The method further involves biasing the second member away from the first member, thereby providing a force to retain the fulcrum body between the first metatarsal and a second metatarsal. In addition, the method involves preparing an end of the first metatarsal, preparing an end of a medial cuneiform opposing the end of the first metatarsal, and moving the first metatarsal toward the second metatarsal in a transverse plane, thereby pivoting the first metatarsal about the fulcrum and reducing an intermetatarsal angle between the first metatarsal and the second metatarsal.

The details of one or more examples are set forth in the accompanying drawings and the description below. Other features, objects, and advantages will be apparent from the description and drawings, and from the claims.

BRIEF DESCRIPTION OF DRAWINGS

FIGS. 1A and 1B are front views of a foot showing a normal first metatarsal position and an example frontal plane rotational misalignment position, respectively.

FIGS. 3A and 3B are side views of a foot showing a normal first metatarsal position and an example sagittal plane misalignment position, respectively.

DETAILED DESCRIPTION

In general, the present disclosure is directed to fulcrum devices that can be used in a surgical procedure, such as bone realignment procedure. Example procedures in which the fulcrum structures may be used include a bone alignment, osteotomy, fusion procedure, and/or other procedures where one or more bones are operated upon and/or realigned relative to one or more other bones. Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing a fulcrum can be performed to correct an alignment between a metatarsal (e.g., a first metatarsal) and a second metatarsal and/or a cuneiform (e.g., a medial, or first, cuneiform), such as in a bunion correction surgery. An example of such a procedure is a Lapidus procedure (also known as a first tarsal-metatarsal fusion). While the example fulcrum structures of the disclosure are generally described as being useful for insertion into an intermetatarsal space to establish and/or maintain a separation gap between the metatarsals while the first metatarsal is being realigned, the fulcrum structures may be used in any desired application and the disclosure is not limited in this respect.

Figure 2B:
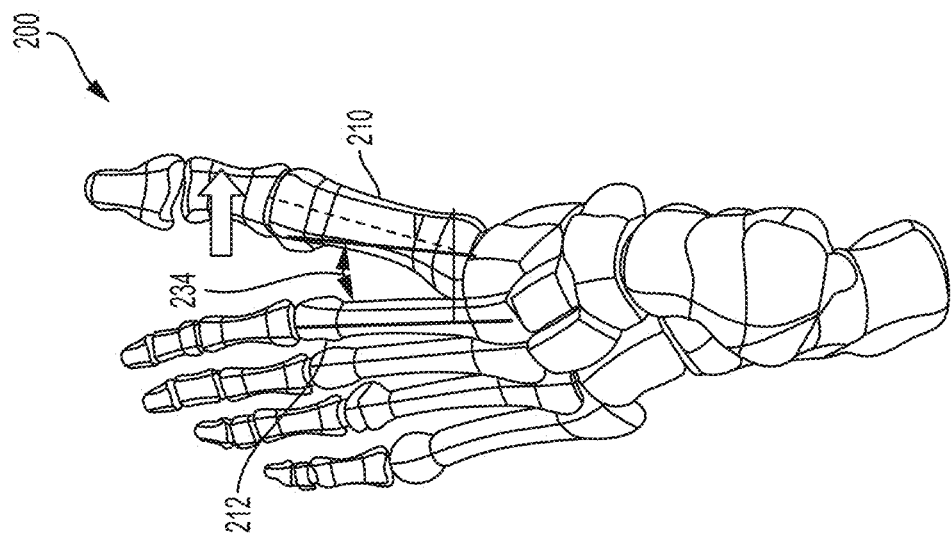
FIGS. 2A and 2B are top views of a foot showing a normal first metatarsal position and an example transverse plane misalignment position, respectively.
Figure 2A:
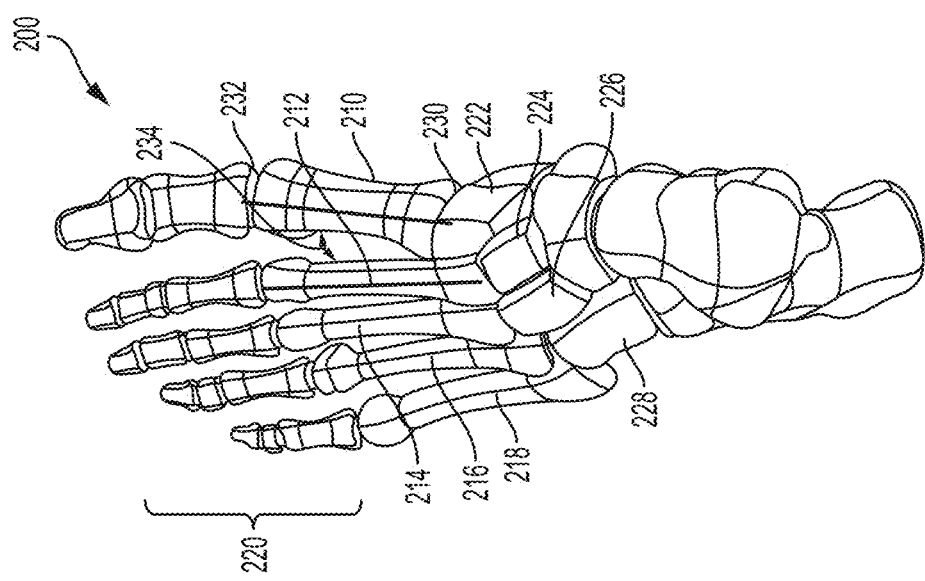

FIGS. 1-3 are different views of a foot 200 showing example anatomical misalignments that may occur and be corrected using a fulcrum according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

A fulcrum according to the disclosure can be used as part of a bone positioning technique to correct an anatomical misalignment of a bone or bones. In some applications, the technique involves realigning a metatarsal, relative to an adjacent cuneiform and/or adjacent metatarsal. The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal or portion thereof for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal.

In some applications, a fulcrum is used as part of a realignment technique to anatomically align first metatarsal 210 or a portion thereof by reducing the IMA from over 10 degrees to about 10 degrees or less (e.g., to an IMA of about 1-5 degrees), including to negative angles of about -5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal is axially rotated between about 4 degrees to about 30 degrees or more. In some embodiments, a fulcrum is used as part of a realignment technique to anatomically align the metatarsal by reducing the metatarsal rotation from about 4 degrees or more to less than 4 degrees (e.g., to about 0 to 2 degrees) by rotating the metatarsal with respect to the medial cuneiform.

A fulcrum according to the disclosure may be useful to provide a structure about which rotation and/or pivoting of one bone relative to another bone occurs. The fulcrum can establish and/or maintain space between adjacent bones being moved, preventing lateral translation or base shift of the bones during rotation and/or pivoting. For example, to help avoid the proximal-most base of the first metatarsal 210 from shifting toward the proximal-most base of the second 212, a clinician can insert the fulcrum in the notch between first metatarsal 210 and second metatarsal 212 at the base of the metatarsals (e.g., adjacent respective cuneiform) before moving the first metatarsal. The fulcrum can provide a point about which first metatarsal 210 can rotate and/or pivot while helping minimize or avoid base compression between the first metatarsal and the second metatarsal. In addition, use of the fulcrum may cause first metatarsal 210 and medial cuneiform 230 to be better angled relative to guide slots positioned over the end faces of the bones, providing a better cut angle through the guide slots than without use of the fulcrum. This can help reduce or eliminate unwanted springback, or return positioning, of first metatarsal 210 after initial realignment of the metatarsal.

Figure 4:
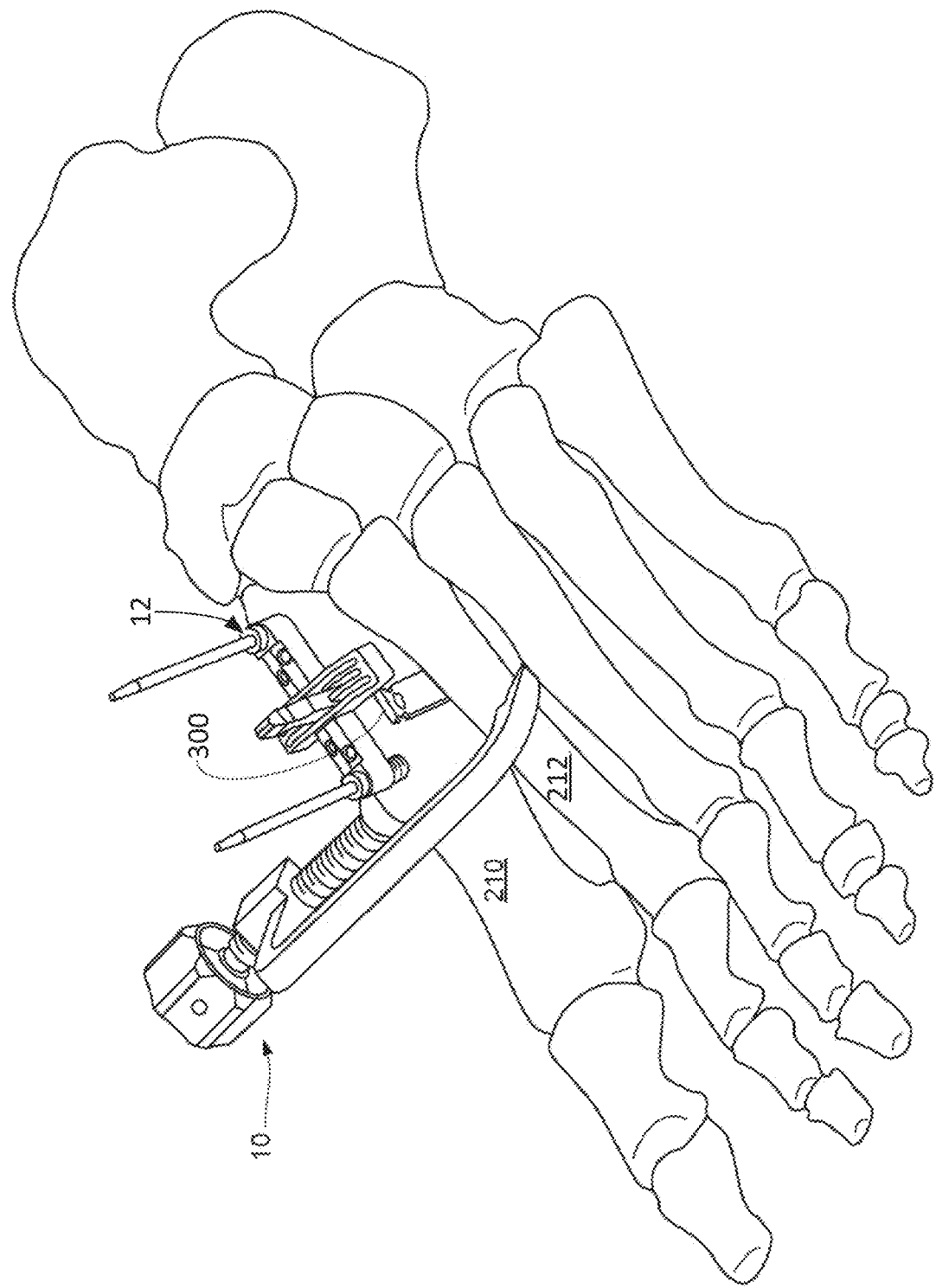
FIG. 4 illustrates an example bone positioning operation in which a fulcrum is positioned at an intersection between a first bone and a second bone.

FIG. 4 illustrates an example bone positioning operation in which a fulcrum 300 is positioned at an intersection between a first bone and a second bone, where the first bone is being to be realigned relative to the second bone. In particular, FIG. 4 illustrates fulcrum 300 being positioned between first metatarsal 210 and second metatarsal 212. Fulcrum 300 may optionally be used in conjunction with surgical devices, such as a bone positioning guide 10 and a bone preparation guide 12. Additional details on example bone positioning guides, bone preparation guides, and related techniques are described in U.S. patent application Ser. No. 14/981,335, filed Dec. 28, 2015, and U.S. patent application Ser. No. 15/236,464, filed Aug. 14, 2016, the entire contents of which are incorporated herein by reference.

As shown in the example of FIG. 4, fulcrum 300 may be positioned distally of a bone preparation guide 12 between first metatarsal 210 and second metatarsal 212 or, in other applications, proximally of the guide (e.g., at the ends of the first and second metatarsals abutting the medial and intermediate cuneiform bones, respectively). In still other examples, fulcrum 300 can be positioned in the intermetatarsal space between first metatarsal 210 and second metatarsal 212 without using bone positioning guide 10 and/or bone preparation guide 12.

When used, the clinician can insert fulcrum 300 between first metatarsal 210 and second metatarsal 212 (or other adjacent bones, when not performing a metatarsal realignment) at any time prior to moving the first metatarsal (e.g., by actuating bone positioning guide 10 or other means of manipulating the bone). In different embodiments, fulcrum 300 can be inserted between first metatarsal 210 and second metatarsal 212 before or after inserting a joint spacer and/or placing bone preparation guide 12 over the joint being operated upon. In one embodiment, the clinician prepares the joint being operated upon to release soft tissues and/or excise the plantar flare from the base of the first metatarsal 210. Either before or after installing bone positioning guide 10 over adjacent bones, the clinician inserts fulcrum 300 at the joint between the first metatarsal and the second metatarsal. The clinician can subsequently actuate bone positioning guide 10. In the case of a left foot as shown in FIG. 4, actuation of bone positioning guide 10 causes the first metatarsal 210 to rotate counterclockwise in the frontal plane (from the perspective of a patient) and also pivot in the transverse plane about the fulcrum. In the case of a right foot (not shown), actuation causes the first metatarsal to rotate clockwise in the frontal plane (from the perspective of a patient) and also pivot in the transverse plane about the fulcrum. Thus, for both feet, actuation of bone positioning guide 10 can supinate the first metatarsal in the frontal plane and pivot the first metatarsal in the transverse plane about fulcrum 300.

Figure 5A:
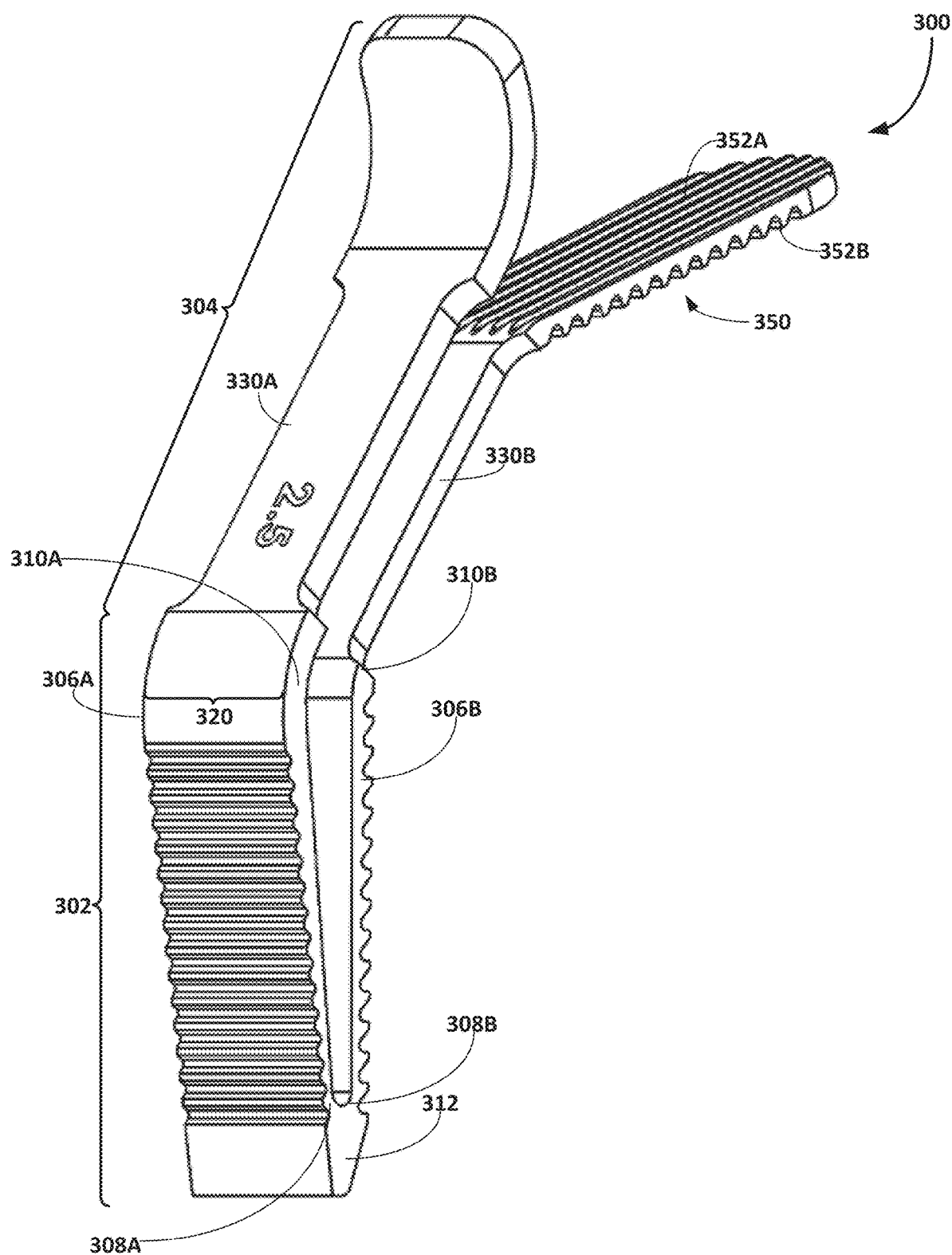
FIGS. 5A and 5B are illustrations of an example configuration of a fulcrum.
Figure 5B:
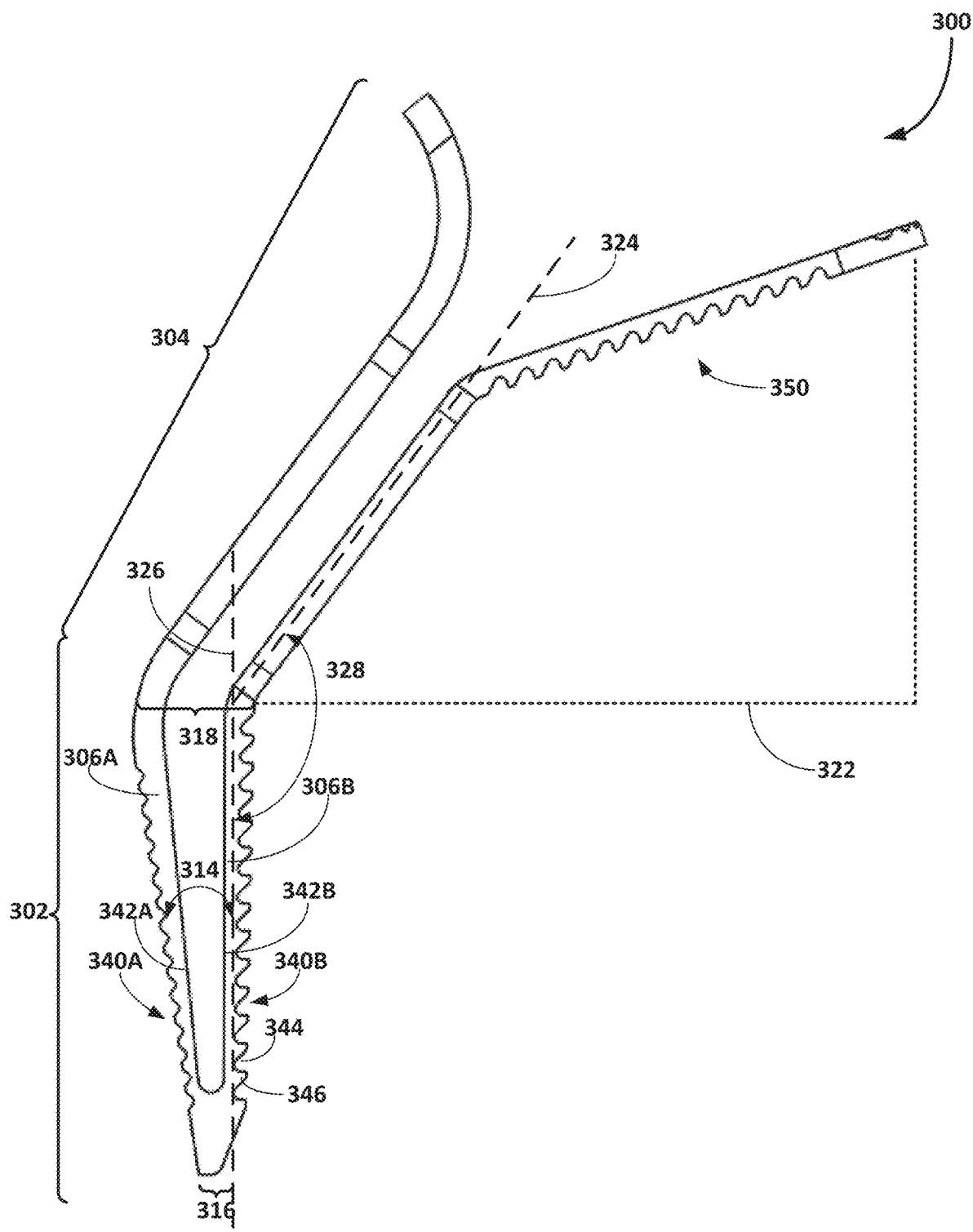

FIGS. 5A and 5B illustrate an example configuration of a fulcrum 300 the can be used according to the present disclosure. FIG. 5A is a perspective view of fulcrum 300, while FIG. 5B is a side view of the fulcrum. In the illustrated configuration, fulcrum 300 includes a body 302 and a handle 304 operatively connected to the body. In some examples, body 302 and handle 304 will be formed as a unitary structure, e.g., by milling, casting, or molding the components to be permanently and structurally integrated together. However, body 302 and handle 304 may be fabricated as separate components that are subsequently joined together.

Body 302 can be configured (e.g., sized and shaped) to be inserted into an intermetatarsal space between adjacent metatarsals. For example, body 302 may be configured to be inserted between a first metatarsal and a second metatarsal. In the illustrated configuration, body 302 is formed by a first elongated member 306A and a second elongated member 306B. The first elongated member 306A has a length extending from a first end 308A to a second end 310A. The second elongated member 306B has a length extending from the first end 308B to a second end 310B. In the illustrated example, the first end 308A of first elongated member 306A is fixedly coupled to the first end 308B of the second elongated member 306B. For example, the first end 308A may be permanently mechanically and/or integrally joined to the first end 308B. In some examples, body 302 extends distally from the first ends 308A and 308B of the first and second elongated members 306A and 306B, respectively, to define a region 312 that is a unitary structure from which first elongated member 306A and second elongated member 306B extend. The thickness of region 312 may be tapered toward the leading end to facilitate insertion of fulcrum 300 into a space between adjacent metatarsals.

In the configuration of FIGS. 5A and 5B, first elongated member 306A is configured to move relative to second elongated member 306B to adjust a thickness of body 302. For example, region 312 coupling first elongated member 306A to second elongated member 306B may provide a spring force that biases the first elongated member away from the second elongated member, for example, when the two members are compressed together. When the second ends 310A and 310B of the first and second elongated members 306A and 306B, respectively, are pressed towards each other, the spring force provided at the opposite first ends 308A and 308B of the elongated members can provide a force biasing the unattached ends back away from each other.

With reference to FIG. 5B, first elongated member 306A is joined to second elongated member 306B with an angle 314 defined between the two elongated members. As a result, body 302 defines a wedge of increasing thickness moving from the first ends 308A and 308B to the second ends 310A and 310B of the two members. The thickness 316 of body 302 may be substantially fixed (e.g., static or unchanging) at the first ends 308A and 308B of the first and second members and/or the distalmost tip of the body. By contrast, the thickness 318 of body 302 may vary at the second end 310A and 310B of the first and second members. The thickness 318 may vary as the ends of the opposed members are moved towards each other (e.g., under a compression force such as hand pressure) or away from each other (e.g., under a biasing spring force provided where the first and second members are joined together).

The angle 314 between the first member 306A and a second member 306B may vary depending on the desired application in which fulcrum 300 is used. In some examples, angle 314 ranges from 0° to 10° when the first and second members 306A and 306B are compressed together, such as from 0° to 5°. When the angle 314 is at 0°, the inner surface of the first member 306A may contact the inner surface of the second member 306B. By contrast, when the angle 314 is at an angle greater than 0°, the inner surface of first member 306A may be separated from the inner surface of the second member 306B by an air gap.

The angle 314 can be greater than 0° when the first and second elongated members are moved away from each other, such as when the spring force provided by the fulcrum biases the first and second members to their natural separation position. In some examples, the angle 314 ranges from greater than 5° to less than 15° when the first and second elongated members are moved away from each other. The separation angles may exist when the first and second members 306A and 306B are at their resting position without a tension force or compression of force applied to the fulcrum.

The thickness of body 302 may vary depending on the desired application in which fulcrum 300 is to be used. In instances in which fulcrum 300 is configured to be inserted in the intermetatarsal space between the first metatarsal and a second metatarsal, the fulcrum may have a size appropriate to be positioned within this anatomical location. In practice, because of the wide variety of different size patients, fulcrum 300 may be offered in multiple different sizes (e.g., as a kit containing multiple different size fulcrums), which allows the clinician to select a particular size fulcrum for the particular application. In some examples, fulcrum 300 has a thickness 318—for example measure at the location of maximum thickness of body 302 in the uncompressed state—that is within a range from 1.5 mm to 15 mm when the first and second members 306A and 306B are moved away from each other (e.g., without a tension or compression force applied to the members), such as from 2.5 mm to 5 mm. When the first and second elongated members 306A and 306B are compressed towards each other to the maximum extent permitted by body 302, thickness 318 may range from 1 mm to 10 mm, such as from 1.5 mm to 3.5 mm. When the interfaces of the first and second elongated members 306A and 306B contact each other when compressed together, the thickness 318 may be the combined thicknesses of the individual first and second members. The individual thickness of first elongated member 306A may be the same as or different than second elongated member 306B.

While the specific dimensions of fulcrum body 302 can vary as noted above, in some examples, the body has a width 320 within a range from 3 millimeters to 30 millimeters, such as from 6 millimeters to 10 millimeters. The body may have a length ranging from 10 millimeters to 60 millimeters, such as from 15 millimeters to 30 millimeters. Such dimensions may be useful for configuring the fulcrum body to be insertable into an intermetatarsal space, although other dimensions can be used.

As noted above, fulcrum 300 may provide a biasing force that pushes the first and second elongated members 306A and 306B away from each other (e.g., at their second ends 310A and 310B). This biasing force causes the individual elongated members to press against respective metatarsals when inserted into the intermetatarsal space, providing a force that helps retain the fulcrum in the intermetatarsal space. The force provided by the fulcrum biasing the first and second elongated members 306A and 306B away from each other may be effective to retain body 302 in the intermetatarsal space, when the body is inserted between adjacent metatarsals of the human foot. In some examples, such as the example illustrated in FIGS. 5A and 5B, the spring force provided by fulcrum 300 is built into the mechanical structure of body 302 based on how the first and second elongated members 306A and 306B are joined together. In other examples, fulcrum 300 may include a torsion spring or other biasing member positioned between the first and second elongated members 306A and 306B (e.g., between the interfaces of the two members) to bias the members away from each other.

In general, fulcrum 300 can be fabricated from any suitable materials. The material(s) used to fabricate the fulcrum may be selected to provide a spring force at the junction 312 between the first elongated member 306A and the second elongated member 306B. Such material may allow the two members to be compressed towards each other, for example under application of human hand pressure, while also allowing the two members to recover to toward their natural position in which the members are separate from each other. In different examples, fulcrum 300 may be fabricated from metal, a polymeric material, or a hybrid form of multiple metals and/or polymeric materials. In addition, although body 302 and handle 304 is generally illustrated as having a rectangular cross-sectional shape, the members forming the body and handle can define a different generally polygonal cross-sectional shape (e.g., square, hexagonal) and/or generally arcuate cross-sectional shape (e.g., circular, elliptical).

As noted above, fulcrum 300 includes handle 304. Handle 304 may be any structure projecting proximally from body 302 that can provide a gripping location for the fulcrum during use. In some examples, such as the example illustrated in FIGS. 5A and 5B, handle 304 can project angularly away from body 302 to define a tissue retraction space 322. Tissue retraction space 322 may be a region bounded on one side by second elongated member 306B and one side of handle 304. In use, fulcrum 300 may be inserted into an intermetatarsal space with handle 304 extending out of the surgical incision and over an epidermal layer with tissue captured in tissue retraction space 322. For example, fulcrum 300 may be inserted into an intermetatarsal space with handle 304 projecting toward the lateral side of the foot being operated upon. Tissue retraction space 322 may help retract tissue and push the tissue laterally away from a first metatarsal and/or medial cuneiform being operated upon.

To form tissue retraction space 322, handle 304 may project away from body 302, e.g., linearly at a zero degree angle or laterally at a non-zero degree angle. The specific angular orientation of the handle 304 relative to the body 302 may vary. However, in some examples, handle 304 is oriented relative to the body 302 so a handle axis 324 intersects an axis 326 extending along the length of the body at an acute angle 328 ranging from 5 degrees to 85 degrees, such as from 20 degrees to 75 degrees, or from 35 degrees to 55 degrees. Handle 304 may be composed of a single linear portion that intersects body 302 at a specific angular orientation or may be composed of multiple linear portions oriented at different angles relative to each other. Moreover, while handle 304 may project away from body 302 at a non-zero degree angle, in other configurations, handle 304 projects at a zero degree angle away from the body. In these configurations, handle 304 may be co-linear with body 302 such that there is no angular offset between the handle and the body.

In the illustrated configuration, handle 304 includes a first handle portion 330A and the second handle portion 330B. The first handle portion 330A is attached to the first elongated member 306A, and the second handle portion 330 B is attached to the second elongated member 306B. In particular, in the illustrated configuration, first handle portion 330A is attached to the second end 310A of first elongated member 306A and second handle portion 330 B is attached to the second end 310 B of second elongated member 306B. Accordingly, there is one handle portion corresponding to each elongated member in this configuration.

The first handle portion 330A and the second handle portion 330 B project angularly in the same direction away from body 302 in the example of FIGS. 5A and 5B. In this configuration, first handle portion 330A and second handle portion 330 B are parallel to each other and separated by an air gap (e.g., of substantially constant thickness) in the uncompressed state. In other examples, such as that described with respect to FIGS. 6A and 6B, handle portions project in different directions away from body 302 relative to each other.

In use, a clinician may grasp the external surfaces of first handle portion 330A and second handle portion 330B and press the two portions towards each other. This can cause the second end 310A of the first elongated member and the second end 310 B of the second elongated member to move toward each other (optionally such that the inner surfaces of the members contact each other) reducing the cross-sectional thickness of body 302. While holding fulcrum 300 in a compressed state, the clinician can insert the fulcrum into the intermetatarsal space and thereafter release the handle portions, causing the first and second elongated members to spring away from each other and press against respective first and second metatarsal.

In the configuration of FIGS. 5A and 5B, fulcrum 300 includes a second body 350 positioned at the opposite end of second handle portion 330 B from the end connected to second elongated member 306B. Fulcrum body 350 may provide an independent fulcrum structure that can be inserted in an intermetatarsal space instead of body 302. Fulcrum body 350 is shown as projecting at a non-zero degree angle away from the second end of second handle portion 330 B, such as an angle ranging from 25° to 75°. Fulcrum body 350 may be substantially planar and have a first surface 352A configured to be positioned in contact with the first metatarsal and a second surface 352B opposite the first surface configured to be positioned in contact with a second metatarsal.

Fulcrum body 350 may be of a different size (e.g., thickness, with, and/or length) then full from body 302. The size of fulcrum body 350 may be within the ranges discussed above as being suitable example sizes for body 302. In use, the clinician may select one fulcrum body over the other fulcrum body based on the anatomy (e.g., intermetatarsal space sizing) of the patient undergoing a surgical procedure and/or may use the different fulcrum bodies at different points in the procedure. For example, the clinician may initially insert planar fulcrum body 350 into the intermetatarsal space to help open the space. The clinician may subsequently retract fulcrum body 350 from the intermetatarsal space, compress fulcrum body 302, and thereafter insert fulcrum body 302 into the intermetatarsal space through the opening created by fulcrum body 350. In some examples, fulcrum body 350 has a thickness that tapers from thicker to thinner toward the leading end of the body, while in other examples, the fulcrum body may have a substantially constant thickness across its length. In still other examples, fulcrum 300 does not include a second fulcrum body but may only include body 302, or may instead include more than two fulcrum bodies, such as one projecting from first handle portion 330A, a second one projecting from handle portion 330B, along with the main fulcrum body 302.

Each elongated member 306A and 306B may have a bone contacting face configured to be positioned in contact with a bone when inserted into an intermetatarsal space. For example, with reference to FIG. 5B, first elongated member 306A has an outward face 340A and it inward face 342A on an opposite side of the elongated member. Similarly, second elongated member 306B has an outward face 340B and it inward face 342B on an opposite side of the elongated member. The outward faces 340A and 340B are positioned to contact first and second metatarsals, respectively, when body 302 is inserted into an intermetatarsal space. The inward faces 342A and 342B are positioned facing each other and, in instances in which body 302 can be fully compressed, can contact each other upon compression.

In some examples, the outward faces 340A and 340B of the first and second members 306A and 306B, respectively, are configured to inhibit and/or facilitate relative motion between a bone and the respective bone-contacting face. Outward face 340A of first member 306A may have surface features which allow the contacting metatarsal (e.g., first metatarsal) to rotate in the frontal plane while contacting the outward face but inhibit movement of the metatarsal in the proximal to distal direction. The surface features may be implemented as ribs and/or grooves, such as multiple grooves extending lengthwise or widthwise across the outward face 340A. The inward faces 342A and 342B of the first and second elongated members may be flat (e.g., planar and/or devoid of surface features) or may have their own texturing.

Outward face 340B may have surface features that inhibit movement between fulcrum 300 and the contacting metatarsal (e.g., second metatarsal) in the dorsal-to-plantar direction. The surface features may be implemented as directionally-oriented ribs and/or grooves. For example, in FIG. 5B, is illustrated as grooves having openings 344 angled upwardly in the dorsal direction. As a result, the backside 346 of the corresponding ribs defining the grooves can slide across the contacting metatarsal (e.g., second metatarsal) as body 302 is inserted plantarly in the intermetatarsal space while the angled openings 344 inhibit inadvertent retraction of the body in the dorsal space, once the body is inserted into the intermetatarsal space. The edges of the grooves defining the angled openings 344 may have a tendency to engage or bite into the metatarsal if elongated body is moved dorsally, thereby inhibiting such movement.

Figure 6A:
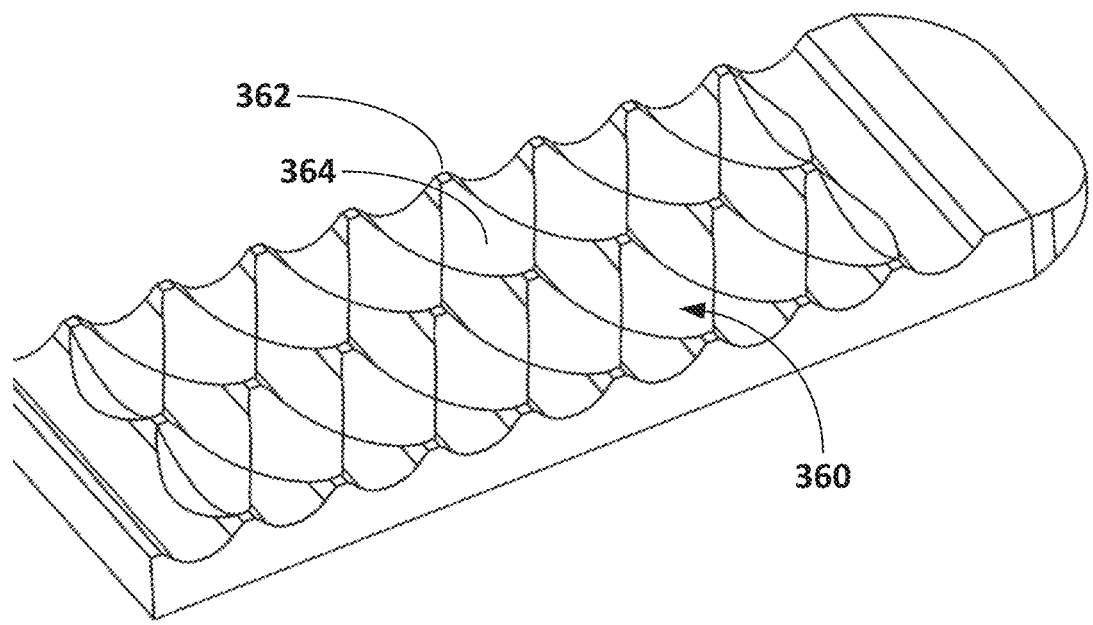
FIGS. 6A-6D are images showing different example surface features that may be used on a fulcrum according to the disclosure.
Figure 6B:
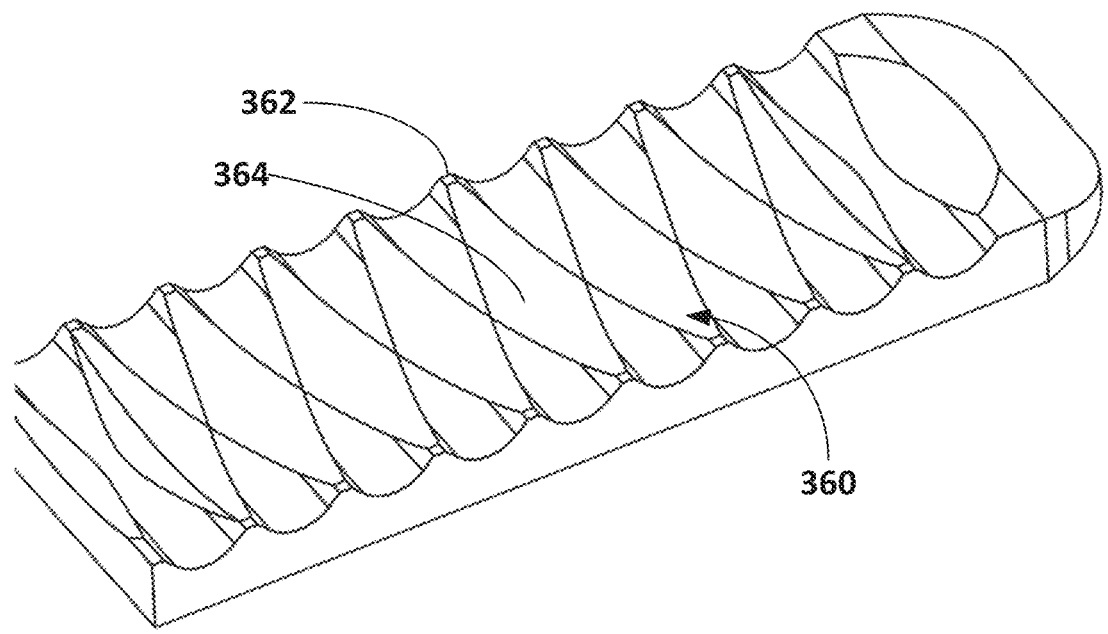

The outward facing surfaces of body 302 may include a variety of different surface features to facilitate efficacious use of the fulcrum. FIGS. 6A-6D are images showing different example surface features that may be used on a fulcrum according to the disclosure. FIG. 6A illustrates an example configuration of surface features 360 defined by intersecting and converging concavities formed in the face of the member. The surface features 360 extend into the face of the elongated member from an apex 362 to a trough 364 and define a radius of curvature. In the illustrated configuration, there are multiple rows of intersecting concavities (particularly two illustrated in FIG. 6A) across the face of the elongated member. By contrast, FIG. 6B illustrates a similar structure of converging concavities formed in the face of the elongated member where there is only a single row of surface features across the face of the structure. The irregular surface structure formed by the converging and adjacent concavities can help inhibit movement of the elongated member in the dorsal to plantar direction and/or the distal to proximal direction. The surface features 360 may have a tendency to bite into the bone in which the surface features are in contact, thereby inhibiting relative movement.

Figure 6C:
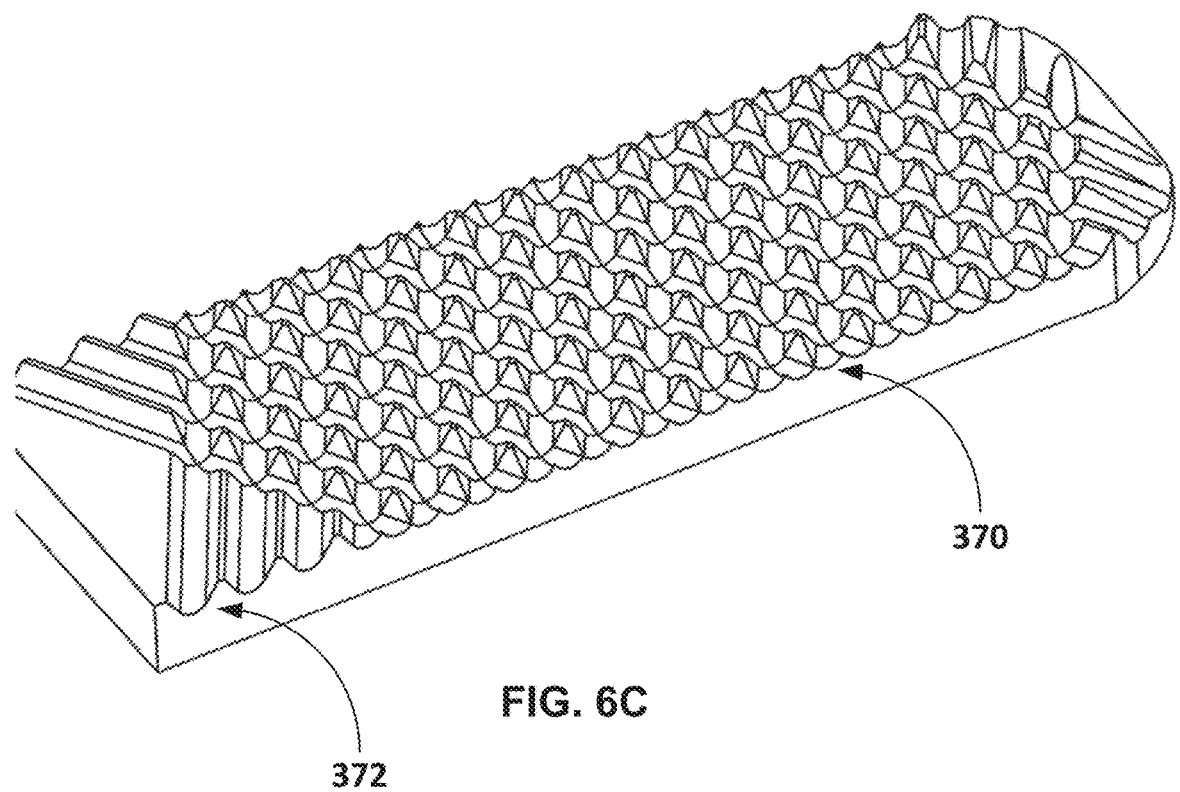

When configured with surface features, the surface features may be the same across the face of the elongated member or different sections of the elongated member may have surface features of different configuration. For example, FIG. 6C illustrates an example configuration of surface features that includes a first set of surface features 370 and a second set of surface features 372. The first set of surface features 370 are defined by a knurling, or a series of intersecting and overlapping ridges. The second set of surface features 372 are defined by angled ribs and grooves that are angled relative to the long axis of the elongated member. In the illustrated configuration, the second set of surface features 372 are positioned on both the leading and trailing edges of the elongated member with the first set of surface features 370 positioned therebetween. However, other configurations and arrangements of multiple surface features may be used. The configuration of the first set of surface features 370 and the second set of surface features 372 can help inhibit movement of the elongated member in the dorsal to plantar direction and/or the distal to proximal direction since the features have a tendency to bite into the bone in which the surface features are in contact, thereby inhibiting relative movement. Accordingly, the example configuration of surface features illustrated in FIGS. 6A-6C may be usefully implemented on the outward face 340B of the second elongated member, which contacts the second metatarsal.

Figure 6D:
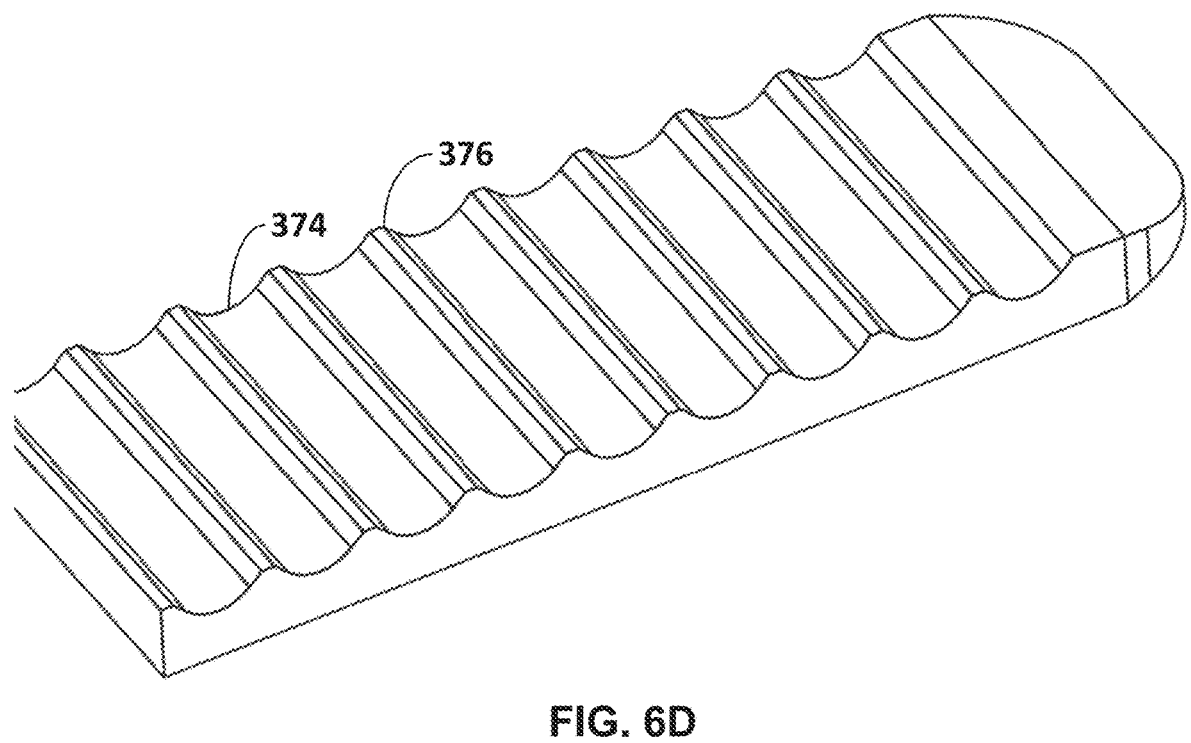

FIG. 6D illustrates an example set of surface features formed by corresponding grooves 374 and ribs 376 that extend across the width of the elongated member. Such a configuration of surface features may be usefully implemented on the outward surface 340A of the first elongated member, as the surface features may allow the first metatarsal in contact with such outward face to be rotated in the frontal plane during realignment. Other configurations of surface features can be used and, in some examples, the outward faces of the fulcrum may not have surface features but may instead be untextured planar surfaces. It should be appreciated therefore that the disclosure is not limited in this respect.

As discussed above, a fulcrum according to the disclosure may have multiple fulcrum bodies, such as fulcrum body 302 and second fulcrum body 350. When so configured, the second fulcrum body 350 may or may not include surface features such as those discussed above in connection with the main fulcrum body. Thus, the exemplary surface features may be applied to the outward surface of any fulcrum body or multiple fulcrum bodies on a particular fulcrum instrument.

Figure 7A:
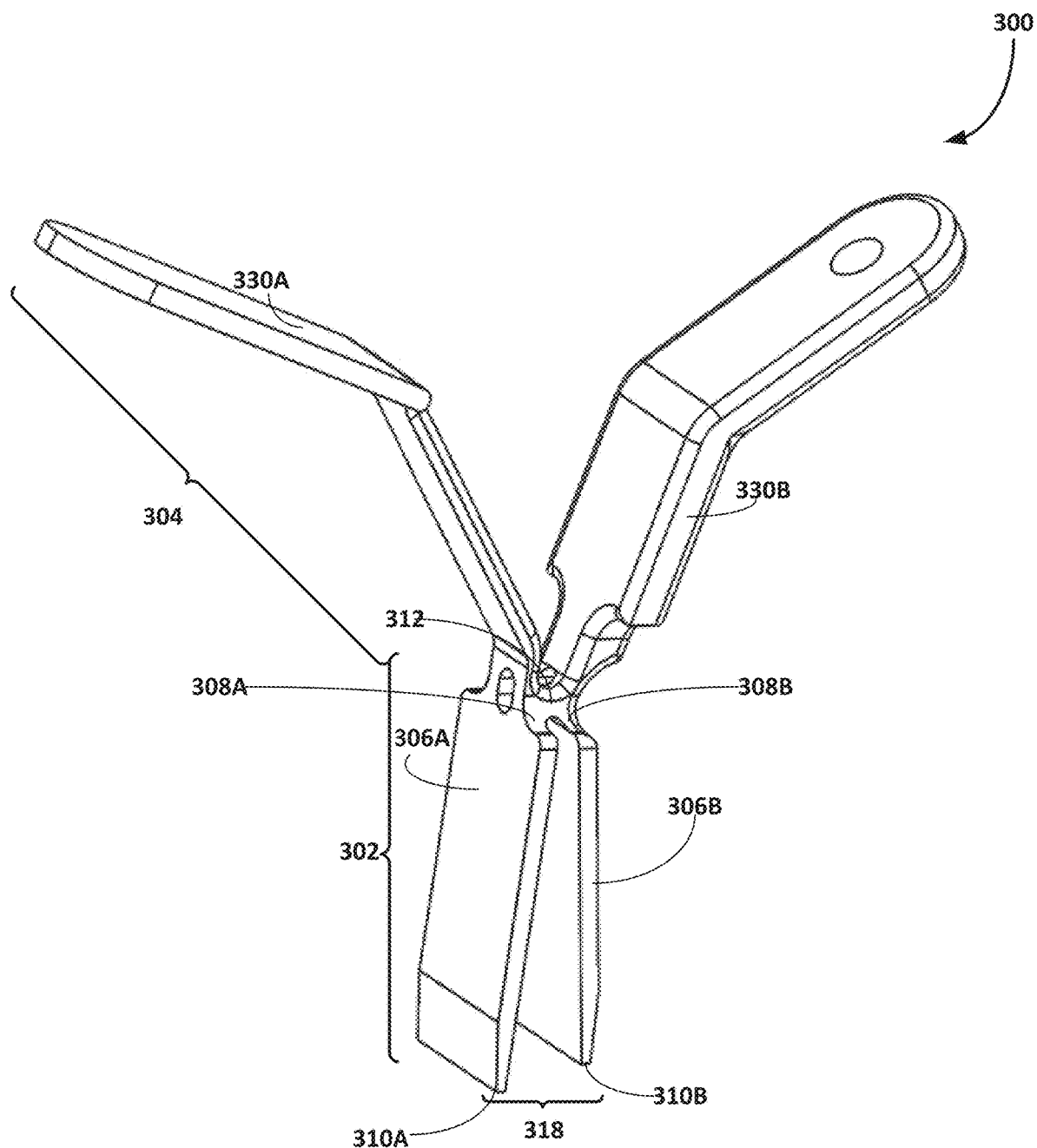
FIGS. 7A and 7B are illustrations of another example configuration of a fulcrum.
Figure 7B:
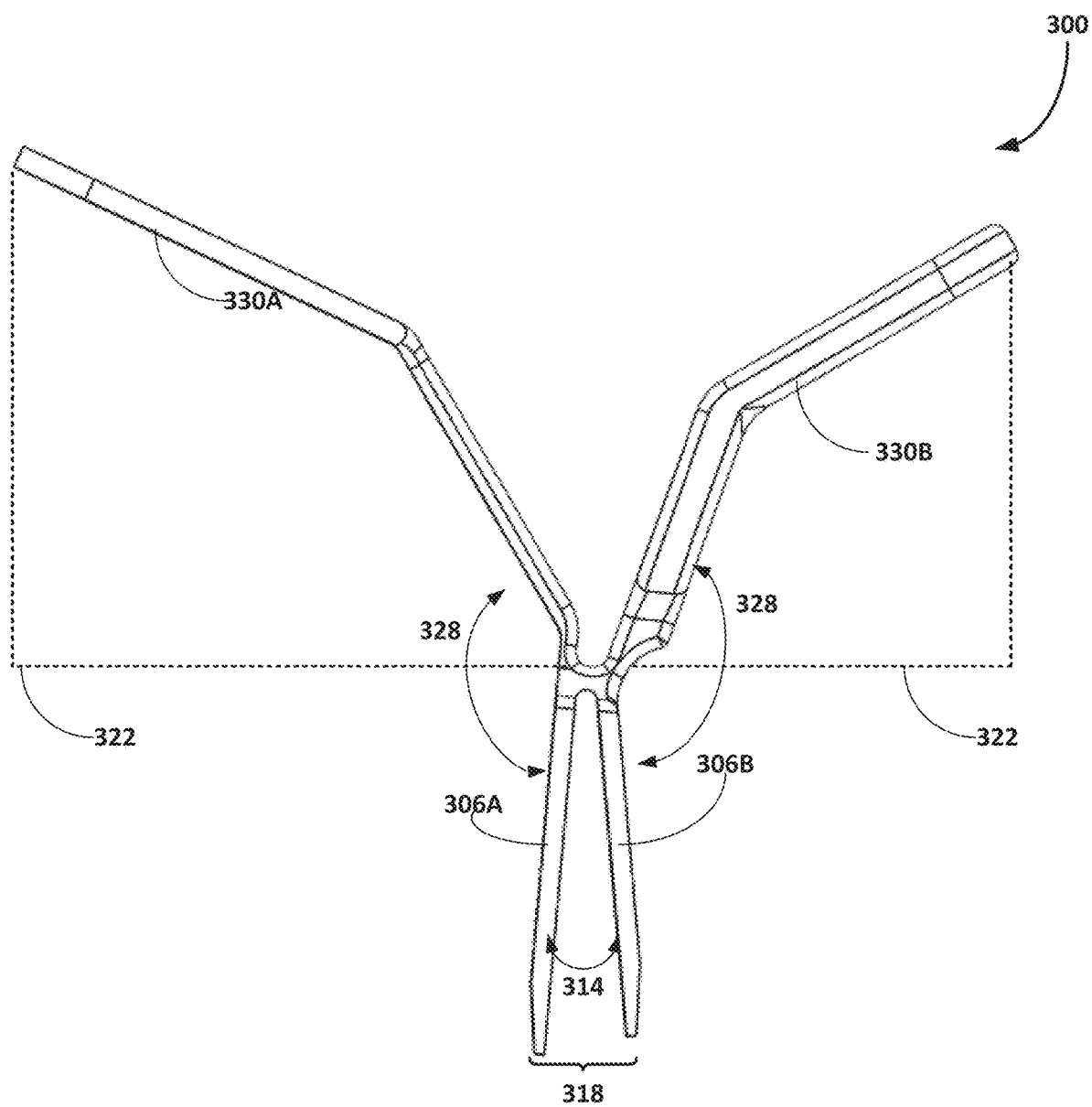

A fulcrum according to the disclosure can have a variety of different configurations that help the fulcrum self-retain within the space in which it is inserted. FIGS. 7A and 7B are illustrations of another example configuration of fulcrum 300 according to the disclosure. FIG. 7A is a perspective view of fulcrum 300, while FIG. 7B is a side view of the fulcrum. Like reference numbers used in FIGS. 7A and 7B to those discussed above with respect to FIGS. 5A and 5B refer to like elements. Accordingly, the discussion of different structural configurations, arrangements, and alternatives provided above with respect to FIGS. 5A and 5B apply to corresponding elements in the configuration of FIGS. 7A and 7B.

As shown in FIGS. 7A and 7B, the configuration of the fulcrum differs in this embodiment than the one illustrated in FIGS. 5A and 5B in that first and second elongated members 306A and 306B are joined at their proximal end and separated at their distal or plantarly-directed end. Accordingly, in FIGS. 7A and 7B, the first end 308A of the first elongated member 306A and the first end 308B of the second elongated member 306B are designated as being on the proximal end of body 302, where the body joins the handle 304. In this configuration, fulcrum 300 has a central connection point where the first elongated member 306A, the second elongated member 306B, the first handle portion 330A, and the second handle portion 330B all join. The junction between the first elongated member 306A and the second elongated member 306B can provide a spring force that biases the second end 310A and 310B of the members away from each other. Additionally or alternatively, and as discussed above with respect to FIGS. 5A and 5B, a torsion spring or other spring member may be inserted between the first and second elongated members.

In operation, a clinician may move first handle portion 330A and second handle portion 330B away from each other, for example the pressing the handle portions downwardly away from each other in a plantar direction. This can cause the second ends 310A and 310B of the first and second elongated members to move towards each other. In some examples, the first and second elongated members can pivot about their junction in amount sufficient to cause the second ends 310A and 310B of the members to come into contact between the two members. In either case, the first and second elongated members 306A and 306B may close an amount effective to allow the fulcrum body 302 to be inserted into and intermetatarsal space between the first metatarsal and a second metatarsal. Upon inserting the fulcrum body a suitable distance into the intermetatarsal space, the clinician may release the hand pressure applied to the first and second handle portions 330A and 330B, allowing the second ends of the elongated members to spring away from each other. This spring force may cause the first and second elongated members to bear against respective first and second metatarsals, helping to retain the fulcrum within the intermetatarsal space.

In the illustrated configuration, first handle portion 330A and second handle portion 330B project in opposite directions away from the body. This can be useful to arrange the handle portions to be further moved in opposite directions away from each other, e.g., downwardly, during use to compress the second ends of the first and second elongated members towards each other. That being said, in other configurations, the handle portions may project in different directions than is illustrated, or fulcrum 300 may not even have handle portions.

Moreover, FIG. 7A illustrates one or more apertures extending through second handle portion 330B. Such an aperture may be used to pin fulcrum 300 at the surgical site being operated on by inserting a pin through the aperture and into tissue or bone underlying the aperture. This can help further secure the fulcrum within the surgical site. First handle portion 330A may also include one or more such apertures. Further, while illustrated in the embodiment of FIG. 7A, any fulcrum embodiment according to the disclosure may include such features.

In addition, although first elongated member 306A and second elongated member 306B are not illustrated as having surface features, it should be appreciated that one or both members may be configured with surface features as described above. In addition, and as further discussed above, one or more handle portions of fulcrum 300 in the example of FIGS. 7A and 7B may be configured with an additional fulcrum body, such as fulcrum body 350.

Figure 8A:
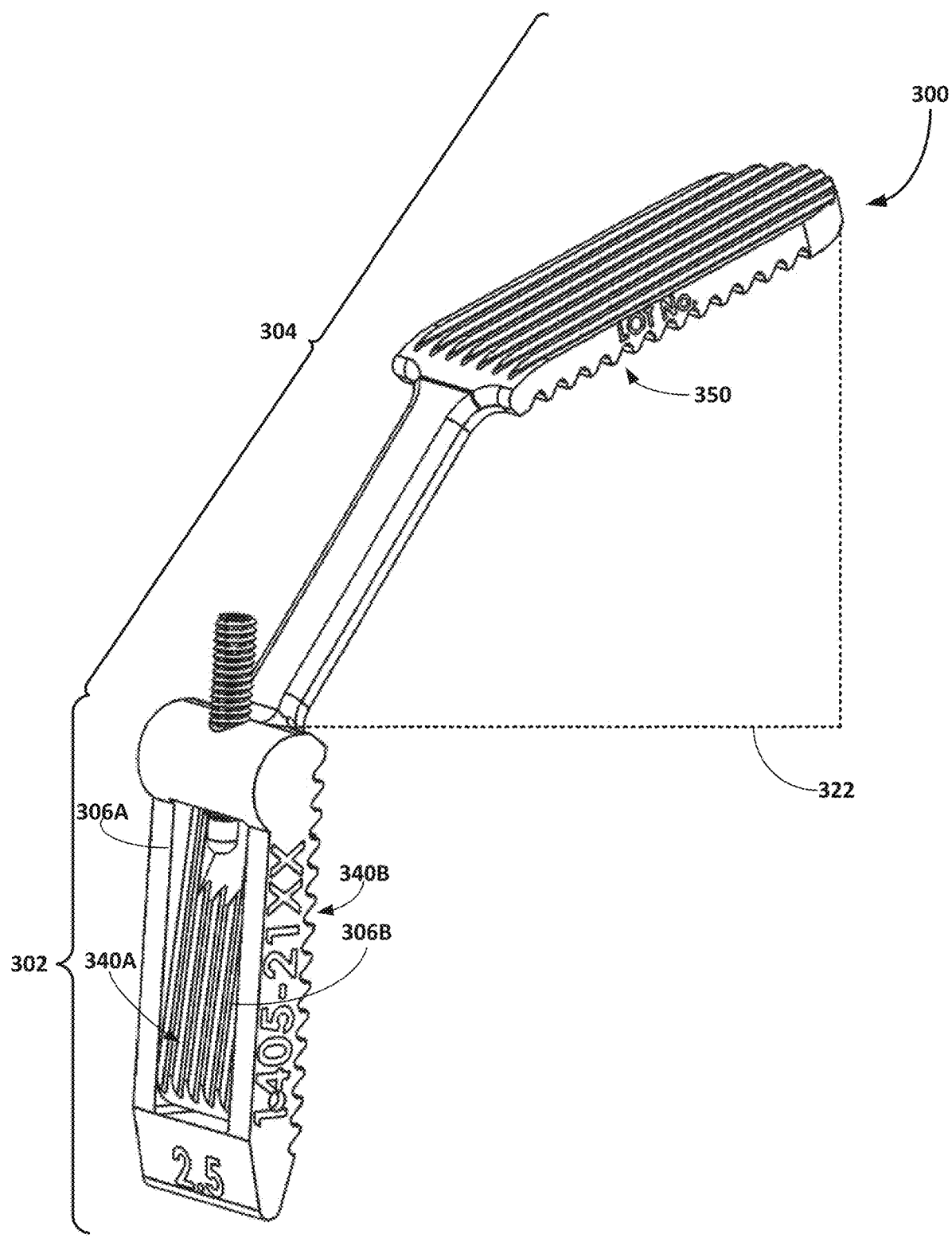
FIGS. 8A and 8B are illustrations of yet another example configuration of a fulcrum.
Figure 8B:
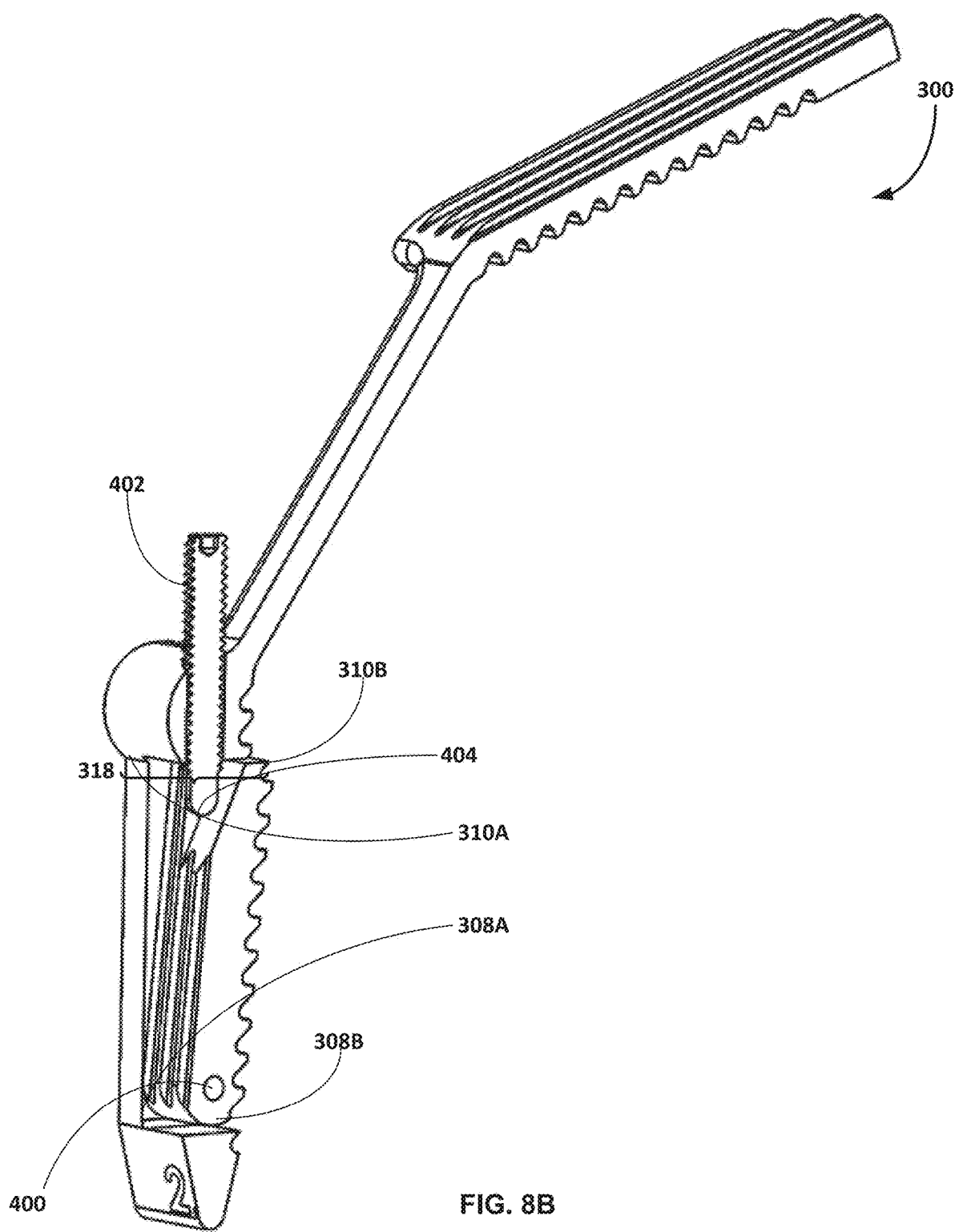

FIGS. 8A and 8B are illustrations of yet another example configuration of fulcrum 300 according to the disclosure. FIG. 8A is a perspective view of fulcrum 300, while FIG. 8B is a sectional side view of the fulcrum. Like reference numbers used in FIGS. 8A and 8B to those discussed above with respect to FIGS. 5A and 5B refer to like elements. Accordingly, the discussion of different structural configurations, arrangements, and alternatives provided above with respect to FIGS. 5A and 5B apply to corresponding elements in the configuration of FIGS. 8A and 8B.

As shown in this example, fulcrum 300 is formed by first member 306A and second member 306B which are rotatably coupled together about an axis of rotation 400. The axis of rotation may be 400 may be formed by a pin extending across the width of first member 306A and second member 306B, for example to join the two members together. To accommodate retraction and expansion of second member 306B relative to first member 306A to adjust the thickness of body 302, the second member 306B may be retracted into and moved out of a cavity defined in the first member 306A. In the illustrated configuration, first member 306A defines a pocket or opening into which second member 306B is inserted and rotatably coupled. A biasing member 402, which is illustrated as being implemented as a set screw, can bear against a portion of second member 306B to controllably extend and retract the second member out of and into the retaining pocket in the first member 306A.

For example, set screw 402 has a distal or plantar head 404 which may be advanced plantarly to bear against a top or dorsal surface 406 of second member 306B. In operation, set screw 402 may be retracted at least partially, and in some examples fully, out of first member 306A to allow the second member 306B to be retracted within the cavity of the first member. When retracted, the thickness 318 of body 302 may be the same as the thickness of first member 306A. After inserting body 302 into and intermetatarsal space, set screw 402 can be advanced plantarly to cause the head 404 to bear against the second member 306B. This can cause the second end 310B of the second member to push outwardly as the first end 308B of the second member rotates about axis 400. The thickness 318 of body 302 increases as the second end 310B of the second member rotates outwardly away from the second and 310A of the first member 306A, forming a wedge of progressively increasing thickness the farther the set screw 402 is advanced plantarly. The thickness of body 302 and corresponding amount of force biasing the first and second members away from each other can therefore be controlled by the clinician during the procedure by controlling the location of the set screw.

Independent of the specific configuration of fulcrum used, a fulcrum according to the disclosure may be self-retaining. The fulcrum may be self-retaining in that it has a variable thickness across its length and/or has a biasing force tending to advance opposed members away from each other at one end all remaining joined at an opposite end. This force may cause the un-joined ends of the fulcrum to bear against opposed bones and create a frictional force that inhibits movement or disengagement of the fulcrum from the intermetatarsal space.

Figure 9A:
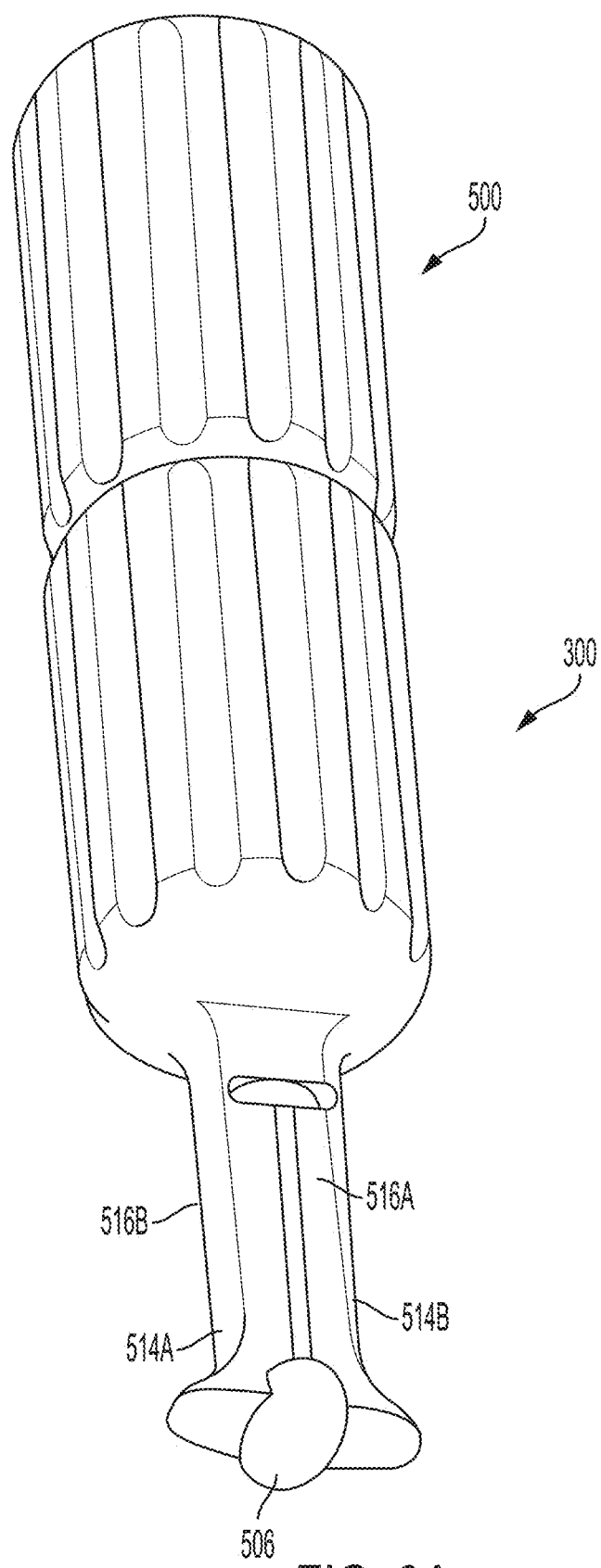
FIGS. 9A-9C are illustrations of an additional example configuration of a fulcrum.
Figure 9C:
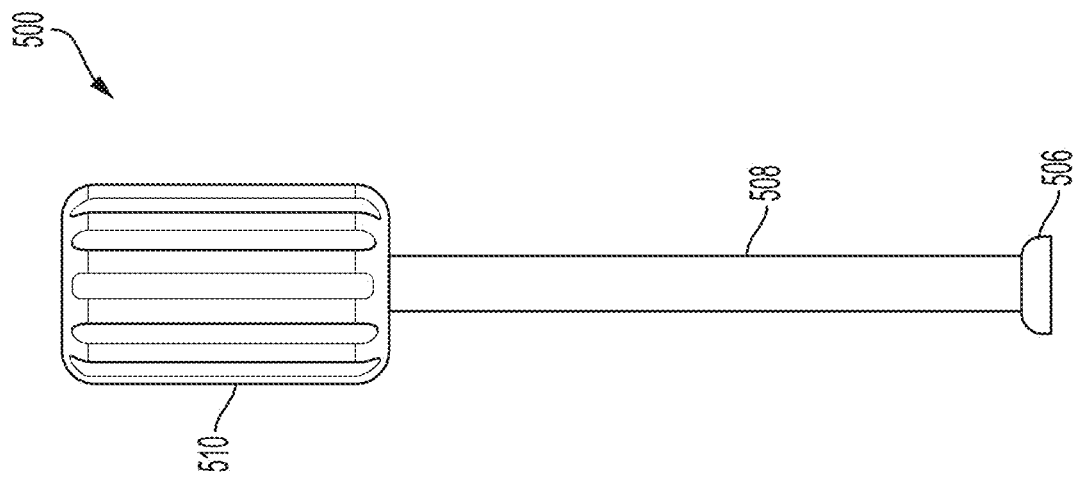
Figure 9B:
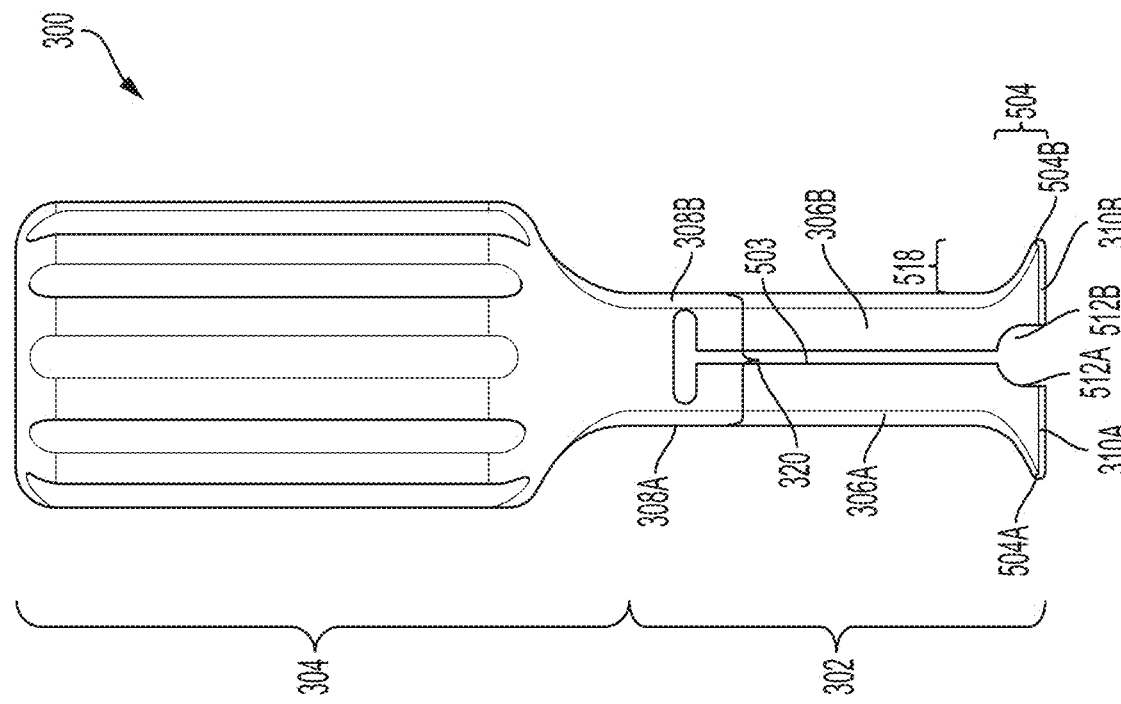

FIGS. 9A-9C are illustrations of another example configuration of fulcrum 300 according to the disclosure. FIG. 9A is a perspective view of fulcrum 300, which is shown engaged with a cam member 500 to control actuation of the fulcrum for retaining within a metatarsal space. FIG. 9B is a side view of fulcrum 300, while FIG. 9C is a side view of cam member 500 that cooperatively engages fulcrum 300. Like reference numbers used in FIGS. 9A-9C to those discussed above refer to like elements.

As shown in FIGS. 9A-9C, fulcrum 300 includes a body 302 operatively connected to a handle 304. Body 302 is formed by first elongated member 306A and second elongated member 306B. The first elongated member 306A has a length extending from first end 308A to second end 310A. The second elongated member 306B has a length extending from first end 308B to second end 310B. Handle 304 is illustrated as being a unitary member from which first elongated member 306A and second elongated member 306B extend and are fixedly coupled. In the illustrated configuration, first end 308A of first elongated member 306A and first end 308B of second elongated member 306B are on the proximal end of body 302, where the body joins the handle 304, whereas the second ends 310A, 310B of the first and second elongated members form the distal end of the body.

First elongated member 306A is separated or divided from second elongated member 306B by a gap or void space 503, which extend axially along the length of the body. In some examples, body 302 includes a foot region 504 of enlarged cross-sectional width relative to a remainder of the body. For example, second end 310A of first elongated member 306A is illustrated as having a first foot 504A, and second end 310B of second elongated member 306B is illustrated as having a second foot 504B. Each foot 504 may be a region that flares or extends outwardly relative to a remaining widest-most section 320 of body 302.

To bias first elongated member 306A away from second elongated member 306B, the fulcrum illustrated in FIGS. 9A-9C is designed to cooperative engage with cam member 500. Cam member 500 can include a cam 506, a cam shaft 508, and a handle 510. Body 302 of fulcrum (e.g., at least one elongated member of the body) can include a cam surface that is configured to interact with cam 506. For example, first elongated member 306A may include a first cam surface 512A, while second elongated member 306B may include a second cam surface 512B. Once assembled, cam member 500 may be operatively engaged with fulcrum 300 to position cam 506 for contact with first and second cam surfaces 512A, 512B.

In use, fulcrum 300 may be inserted into an intermetatarsal space. For example, fulcrum 300 may be rotated so a width 320 of the fulcrum between a first side 514A and a second side 514B of the fulcrum is inline with the intermetatarsal space, e.g., positioning a first major face 516A in contact with a first metatarsal and a second major face 516B in contact with a second metatarsal. Fulcrum can be inserted into the intermetatarsal space (e.g., in a distal to proximal direction and/or a dorsal to plantar direction). After positioning foot region 504 of fulcrum 300 plantarly and/or below the metatarsals within the intermetatarsal space, the fulcrum may be rotated (e.g., 90 degrees) to move first side 514A in contact with one metatarsal and second side 514B in contact with an opposite metatarsal. Rotation may cause foot region 504 to rotate from being position within the intermetatarsal space to having first foot member 504A positioned in contact with a plantar side of a first metatarsal and second foot member 504B positioned in contact with a plantar side of a second metatarsal. Accordingly, foot region 504 may help prevent inadvertent retraction or dislodging of fulcrum 300 during use.

After suitably positioning foot region 504, cam member 500 can be engaged to bias first elongated member 306A away from second elongated member 306B. For example, handle 510 can be rotated (e.g., 90 degrees), causing cam 506 to rotate and push first elongated member 306A away from second elongated member 306B. Cam 506 and/or cam surfaces 512A, 512B may have one or more detent or engagement positions where the cam rotationally locks. For example, in the illustrated configuration of FIG. 9A where cam 506 is oval-shaped and cam surfaces 512A, 512B are arcuate, cam 506 may exhibit locking or detent positions at 90 degree rotational positions.

As noted, fulcrum can be operatively engaged with cam member 500. In the illustrated configuration of FIG. 9A-9C, cam member 500 is show positioned co-axially with fulcrum 300 and rotatable thereto. When so configured, fulcrum 300 (e.g., including body 302 and handle 304) may have an opening extending along a length thereof in which cam member 500 is positioned. Once inserted, cam shaft 508 can extend through handle 304 and along at least a portion of the length of body 302. Handle 502 can be rotated relative to handle 304 to rotate cam 506 relative to cam surfaces 512A, 512B.

The dimensions of fulcrum 300 discussed above with respect to FIGS. 5A and 5B can be used for fulcrum 300 in FIGS. 9A-9C. In some examples, fulcrum 300 has a width 320 (FIG. 9B) in the unexpanded state (e.g., without cam 506 rotationally engaged) ranging from 0.5 mm to 10 mm. Engagement of cam 506 can cause first elongated member 306A and second elongated member 306B to move away from each other, e.g., with the distance of movement being dictated by the size and/or shape of cam 506. In some examples, first elongated member 306A and second elongated member 306B move away from each other a distance ranging from 0.1 mm to 5 mm, such as from 0.5 mm to 2 mm upon engagement of cam 506. Accordingly, in some examples, fulcrum 300 may have a width 320 (FIG. 9B) in the expanded state ranging from 1 mm to 15 mm, such as from 1.5 mm to 3.5 mm.

When configured with foot region 504, each foot may extend a distance 518 away from a remainder of the body 302 a distance ranging from 0.1 mm to 5 mm, such as from 0.5 mm to 2 mm. Foot region 504 may range from 5% of the overall length of body 302 to 25% of the length, or from 1% to 15%, or from 10% to 20%. The foregoing dimensions are merely examples, and the disclosure is not necessarily limited in this effect.

Figure 10A:
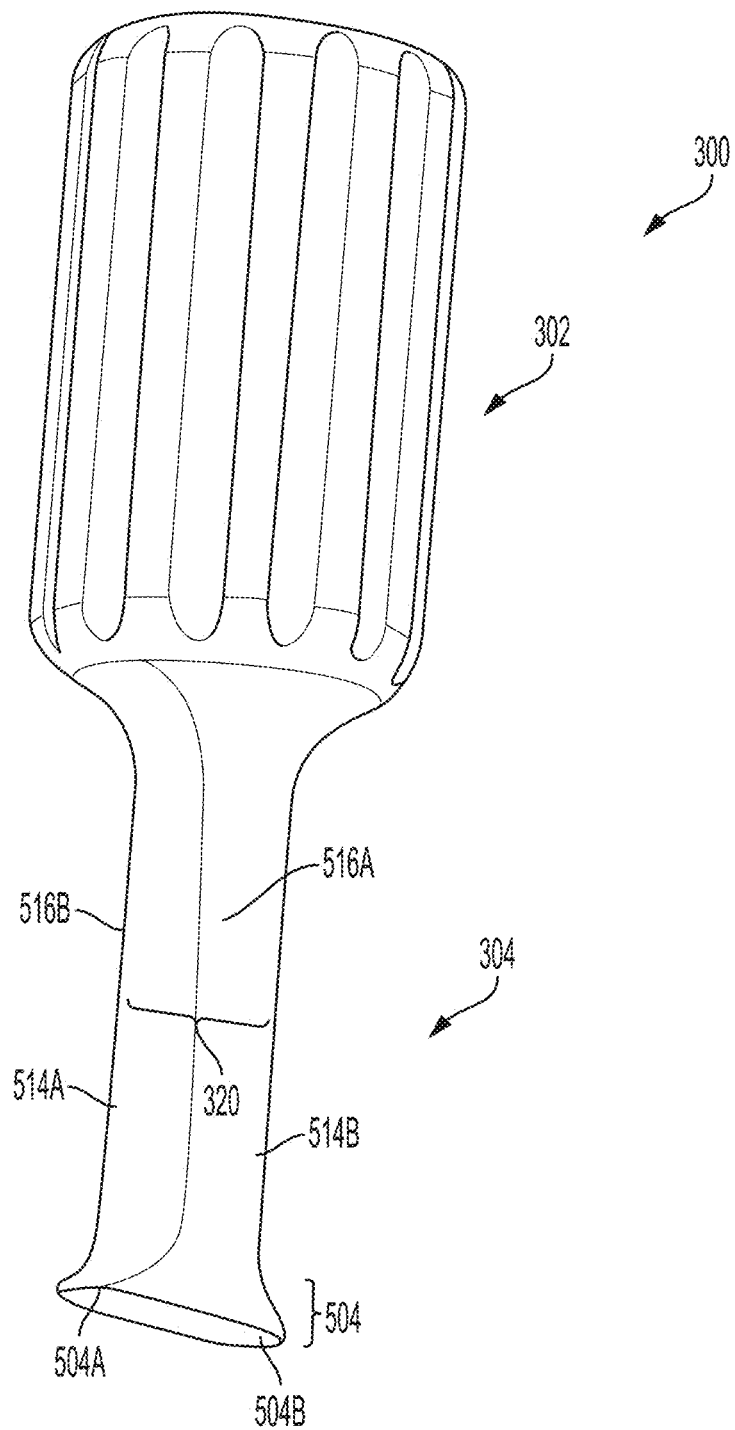
FIGS. 10A and 10B are illustrations of a further example configuration of a fulcrum.
Figure 10B:
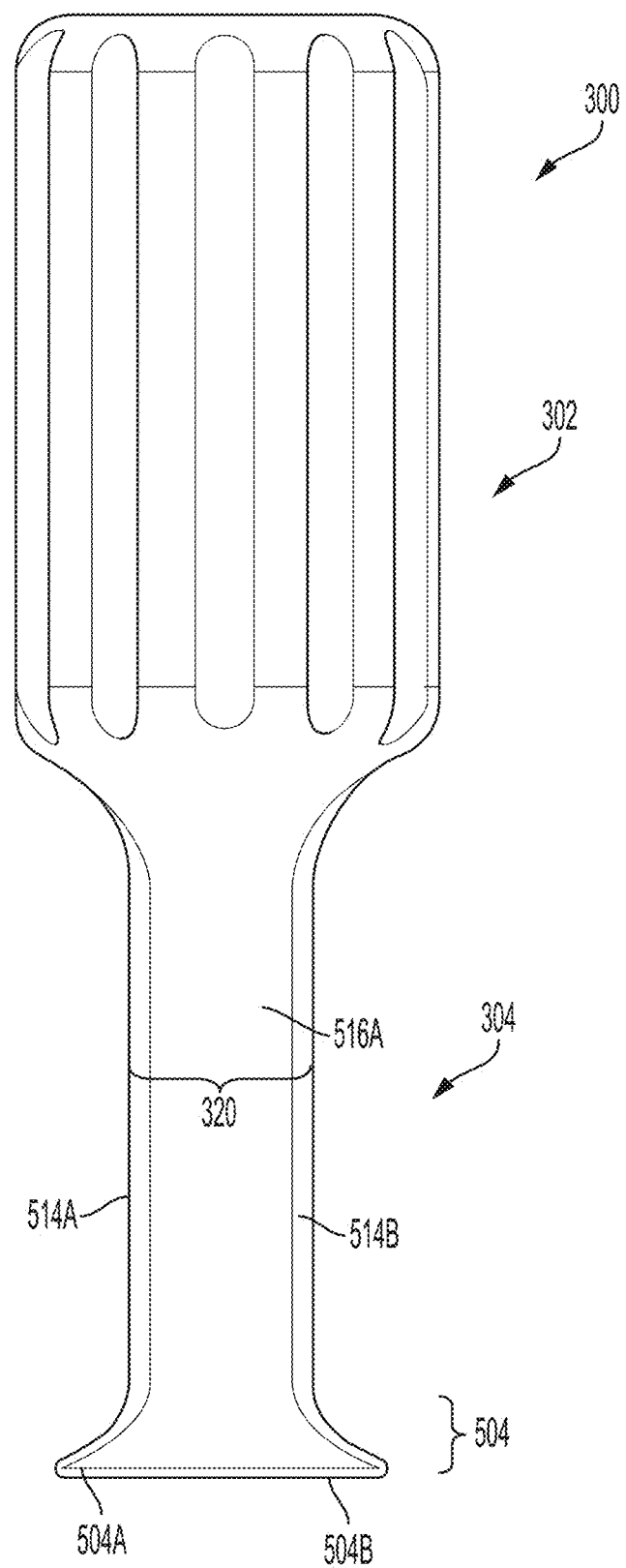

FIGS. 10A and 10B are perspective and side views, respectively, of another example configuration of a fulcrum 300. Fulcrum 300 in FIGS. 10A and 10B includes a body 302 and handle 304, where like reference numerals refer to like elements discussed above. The configuration of the fulcrum in FIGS. 10A and 10B differs from the one illustrated in FIGS. 9A-9C in that body 302 is formed of a single elongated member rather than two elongated members. Further, fulcrum 300 in FIGS. 10A and 10B is not operatively connected to a cam member. Rather, in the configuration of FIGS. 10A and 10B, fulcrum 300 includes a unitary body member that terminates in foot region 504.

In use, fulcrum 300 in FIGS. 10A and 10B may inserted into an intermetatarsal space, e.g., with handle 304 extending out of the surgical incision. For example, fulcrum 300 may be rotated so a width 320 of the fulcrum is inline with the intermetatarsal space, e.g., positioning a first major face 516A in contact with a first metatarsal and a second major face 516B in contact with a second metatarsal. Fulcrum can be inserted into the intermetatarsal space (e.g., in a distal to proximal direction and/or a dorsal to plantar direction). After positioning foot region 504 of fulcrum 300 plantarly below the metatarsals within the intermetatarsal space, the fulcrum may be rotated (e.g., 90 degrees) to move first side 514A in contact with one metatarsal and second side 514B in contact with an opposite metatarsal. Rotation may cause foot region 504 to rotate from being position within the intermetatarsal space to having first foot member 504A positioned in contact with a plantar side of a first metatarsal and second foot member 504B positioned in contact with a plantar side of a second metatarsal. Accordingly, foot region 504 may help prevent inadvertent retraction or dislodging of fulcrum 300 during use. The dimensions of fulcrum 300 discussed above with respect to FIGS. 9A-9C can be used for fulcrum 300 in FIGS. 10A and 10B.

Various examples have been described. These and other examples are within the scope of the following claims.

The invention claimed is:

1. A method comprising:
inserting a fulcrum body comprising a first member and a second member between a first metatarsal and a second metatarsal, wherein the first member comprises a cavity, and the second member is configured to be retracted into and moved out of the cavity;
biasing the second member away from the first member to establish and/or maintain a separation gap between the first metatarsal and the second metatarsal, wherein biasing the second member away from the first member comprises advancing a biasing member into the cavity;
preparing an end of the first metatarsal;
preparing an end of a medial cuneiform opposing the end of the first metatarsal; and
moving the first metatarsal toward the second metatarsal in at least a transverse plane, thereby pivoting the first metatarsal about the fulcrum body and reducing an intermetatarsal angle between the first metatarsal and the second metatarsal.

2. The method of claim 1, wherein the first member has a length extending from a first end to a second end, the second member has a length extending from a first end to a second end, the first end of the second member is coupled to the first member, and the second end of the second member is movable toward and away from the first member such that a thickness of the fulcrum body between the first member and the second member is adjustable.

3. The method of claim 2, wherein first end of the second member is coupled to the first member at an angle such that the fulcrum body defines a wedge of increasing thickness moving from the first end of the first and second members to the second end of the first and second members.

4. The method of claim 3, wherein the intermetatarsal angle ranges from 0 degrees to 10 degrees when the second member is moved toward the first member to greater than 10 degrees when the second member is moved away from the first member.

5. The method of claim 4, wherein the angle is within a range from greater than 0 degrees to less than 15 degrees when the second member is moved away from the first member.

6. The method of claim 2, wherein biasing member is a set screw, and biasing the second member away from the first member comprises advancing the set screw toward the first end of the first member, thereby causing the second end of the second member to move away from the first member.

7. The method of claim 1, further comprising a handle projecting at a non-zero degree angle away from the fulcrum body, wherein inserting the fulcrum body further comprises retracting tissue laterally away from an incision providing access to the first metatarsal and the second metatarsal and holding the tissue away from the incision in a tissue retraction space formed between the handle and the fulcrum body.

8. The method of claim 1, wherein a thickness of the fulcrum body is within a range from 2.5 mm to 10 mm prior to inserting the fulcrum body, and the thickness of the fulcrum body is within a range from 1.5 mm to 3.5 mm when the fulcrum body is inserted between the first metatarsal and the second metatarsal and the second member is biased away from the first member.

9. The method of claim 1, wherein biasing the second member away from the first member comprises expanding the fulcrum body to increase a distance between the first member and the second member.

10. The method of claim 1, further comprising, after moving the first metatarsal toward the second metatarsal in at least the transverse plane, fixating a position of the first metatarsal for fusion.

11. The method of claim 1, wherein moving the first metatarsal toward the second metatarsal the separation gap comprises moving the first metatarsal toward the second metatarsal using a bone positioning guide.

12. The method of claim 1, wherein inserting the fulcrum body between the first metatarsal and the second metatarsal comprises inserting the fulcrum body between the first metatarsal and the second metatarsal after placing a bone preparation guide over a tarsometatarsal joint between the first metatarsal and the medial cuneiform.

13. The method of claim 1, wherein moving the first metatarsal toward the second metatarsal in at least the transverse plane further comprises rotating the first metatarsal toward the second metatarsal in a frontal plane.

14. The method of claim 1, wherein biasing the second member away from the first member to establish and/or maintain in at least the transverse plane between the first metatarsal and the second metatarsal comprises moving the first member and the second member away from each other a distance within a range from 0.1 mm to 5 mm.

15. The method of claim 1, wherein advancing the biasing member into the cavity comprises causing the biasing member to bear against a surface of the second member.

16. The method of claim 15, wherein causing the biasing member to bear against the surface of the second member comprises causing the biasing member to bear against a dorsal surface of the second member.

17. The method of claim 15, wherein the biasing member is a set screw.

* * * * *